United States Patent
Kang et al.

(10) Patent No.: US 11,696,954 B2
(45) Date of Patent: Jul. 11, 2023

(54) SYNTHESIS OF SPHERICAL NUCLEIC ACIDS USING LIPOPHILIC MOIETIES

(71) Applicant: Exicure Operating Company, Chicago, IL (US)

(72) Inventors: Richard Kang, Wilmette, IL (US); Subbarao Nallagatla, Skokie, IL (US); Bart Anderson, Morton Grove, IL (US); Ekambar Kandimalla, Skokie, IL (US)

(73) Assignee: Exicure Operating Company, Chicago, IL (US)

( * ) Notice: Subject to any disclaimer, the term of this patent is extended or adjusted under 35 U.S.C. 154(b) by 8 days.

(21) Appl. No.: 16/608,685

(22) PCT Filed: Apr. 27, 2018

(86) PCT No.: PCT/US2018/030021
§ 371 (c)(1),
(2) Date: Oct. 25, 2019

(87) PCT Pub. No.: WO2018/201090
PCT Pub. Date: Nov. 1, 2018

(65) Prior Publication Data
US 2020/0188521 A1    Jun. 18, 2020

Related U.S. Application Data

(60) Provisional application No. 62/492,062, filed on Apr. 28, 2017.

(51) Int. Cl.
*A61K 47/54*    (2017.01)
*A61P 37/04*    (2006.01)
(Continued)

(52) U.S. Cl.
CPC ............ *A61K 47/549* (2017.08); *A61K 9/127* (2013.01); *A61K 31/7088* (2013.01); *A61K 47/544* (2017.08); *A61P 37/04* (2018.01)

(58) Field of Classification Search
CPC .............................. A61K 9/127; A61K 47/549
See application file for complete search history.

(56) References Cited

U.S. PATENT DOCUMENTS 4,904,582 A    2/1990 Tullis
5,264,618 A    11/1993 Felgner et al.
(Continued)

FOREIGN PATENT DOCUMENTS

CN    1335884 A    2/2002
CN    1341660 A    3/2002
(Continued)

OTHER PUBLICATIONS

Resham J. Banga, Natalia Chernyak, Suguna P. Narayan, SonBinh T. Nguyen, and Chad A. Mirkin. "Liposomal Spherical Nucleic Acids." Journal of the American Chemical Society, vol. 136, 2014, pp. 9866-9869. (Year: 2014).*

(Continued)

*Primary Examiner* — Isaac Shomer
(74) *Attorney, Agent, or Firm* — Wolf, Greenfield & Sacks, P.C.

(57) ABSTRACT

Spherical nucleic acids (SNA) carrying self-aggregating oligonucleotides are described herein. Compositions of the SNA include discrete nanostructures that are not aggregated. Related methods are also described.

13 Claims, 4 Drawing Sheets

Specification includes a Sequence Listing.

(51) Int. Cl.
*A61K 9/127* (2006.01)
*A61K 31/7088* (2006.01)

(56) References Cited

U.S. PATENT DOCUMENTS

| | | |
|---|---|---|
| 5,472,881 A | 12/1995 | Beebe et al. |
| 5,512,439 A | 4/1996 | Hornes et al. |
| 5,578,718 A | 11/1996 | Cook et al. |
| 5,780,448 A | 7/1998 | Davis |
| 5,869,286 A | 2/1999 | Yao et al. |
| 5,955,589 A | 9/1999 | Cook et al. |
| 6,051,698 A | 4/2000 | Janjic et al. |
| 6,072,033 A | 6/2000 | Yao et al. |
| 6,072,037 A | 6/2000 | Yao et al. |
| 6,096,305 A | 8/2000 | Yao et al. |
| 6,100,235 A | 8/2000 | Yao et al. |
| 6,191,104 B1 | 2/2001 | Spriggs et al. |
| 6,194,388 B1 | 2/2001 | Krieg et al. |
| 6,197,525 B1 | 3/2001 | Yao et al. |
| 6,207,646 B1 | 3/2001 | Krieg et al. |
| 6,214,806 B1 | 4/2001 | Krieg et al. |
| 6,218,371 B1 | 4/2001 | Krieg et al. |
| 6,239,116 B1 | 5/2001 | Krieg et al. |
| 6,271,209 B1 | 8/2001 | Smith et al. |
| 6,339,068 B1 | 1/2002 | Krieg et al. |
| 6,361,944 B1 | 3/2002 | Mirkin et al. |
| 6,406,705 B1 | 6/2002 | Davis et al. |
| 6,429,199 B1 | 8/2002 | Krieg et al. |
| 6,482,923 B1 | 11/2002 | Shi et al. |
| 6,506,564 B1 | 1/2003 | Mirkin et al. |
| 6,534,062 B2 | 3/2003 | Raz et al. |
| 6,562,578 B1 | 5/2003 | Gorman et al. |
| 6,569,419 B2 | 5/2003 | Moore et al. |
| 6,569,645 B2 | 5/2003 | Chen et al. |
| 6,579,520 B2 | 6/2003 | Chen et al. |
| 6,610,308 B1 | 8/2003 | Haensler |
| 6,635,443 B1 | 10/2003 | Shi et al. |
| 6,849,719 B2 | 2/2005 | Shi et al. |
| 6,902,735 B1 | 6/2005 | Jacobs et al. |
| 7,094,566 B2 | 8/2006 | Medlock et al. |
| 7,094,886 B2 | 8/2006 | Shaughnessy |
| 7,115,398 B2 | 10/2006 | Chen et al. |
| 7,129,222 B2 | 10/2006 | Van Nest et al. |
| 7,217,412 B2 | 5/2007 | Chen et al. |
| 7,223,741 B2 | 5/2007 | Krieg |
| 7,250,403 B2 | 7/2007 | Van Nest et al. |
| 7,255,868 B2 | 8/2007 | Fearon et al. |
| 7,256,264 B2 | 8/2007 | Goddard et al. |
| 7,276,489 B2 | 10/2007 | Agrawal et al. |
| 7,332,586 B2 | 2/2008 | Franzen et al. |
| 7,404,969 B2 | 7/2008 | Chen et al. |
| 7,427,405 B2 | 9/2008 | Agrawal et al. |
| 7,470,674 B2 | 12/2008 | Agrawal et al. |
| 7,473,763 B2 | 1/2009 | Goddard et al. |
| 7,514,099 B2 | 4/2009 | Chen et al. |
| 7,544,482 B2 | 6/2009 | Goddard et al. |
| 7,563,618 B2 | 7/2009 | Gryaznov et al. |
| 7,611,857 B2 | 11/2009 | Medlock et al. |
| 7,615,539 B2 | 11/2009 | Uhlmann et al. |
| 7,628,990 B2 | 12/2009 | Tuck et al. |
| 7,638,603 B2 | 12/2009 | Shi et al. |
| 7,655,761 B2 | 2/2010 | Gorman et al. |
| 7,666,674 B2 | 2/2010 | Klinman et al. |
| 7,696,150 B2 | 4/2010 | Shaughnessy |
| 7,713,535 B2 | 5/2010 | Agrawal et al. |
| 7,718,397 B2 | 5/2010 | Goddard et al. |
| 7,771,719 B1 | 8/2010 | Filvaroff et al. |
| 7,833,992 B2 | 11/2010 | Vargeese et al. |
| 7,879,980 B2 | 2/2011 | Golstein et al. |
| 7,943,738 B2 | 5/2011 | Medlock et al. |
| 7,956,176 B2 | 6/2011 | McSwiggen et al. |
| 7,964,578 B2 | 6/2011 | Vargeese et al. |
| 7,993,659 B2 | 8/2011 | Noelle et al. |
| 8,008,267 B2 | 8/2011 | Kandimalla et al. |
| 8,058,249 B2 | 11/2011 | Krieg et al. |
| 8,088,388 B2 | 1/2012 | Sokoll |
| 8,124,590 B2 | 2/2012 | Van Nest et al. |
| 8,133,734 B2 | 3/2012 | Shi et al. |
| 8,158,768 B2 | 4/2012 | Dina et al. |
| 8,188,254 B2 | 5/2012 | Uhlmann et al. |
| 8,202,979 B2 | 6/2012 | McSwiggen et al. |
| 8,273,866 B2 | 9/2012 | McSwiggen et al. |
| 8,309,527 B2 | 11/2012 | Krieg et al. |
| 8,323,686 B2 | 12/2012 | Mirkin et al. |
| 8,333,980 B2 | 12/2012 | Van Nest et al. |
| 8,338,132 B2 | 12/2012 | Chen et al. |
| 8,431,544 B1 | 4/2013 | Agrawal et al. |
| 8,455,217 B2 | 6/2013 | Goddard et al. |
| 8,470,342 B2 * | 6/2013 | Klinman ............. A61P 31/06 424/234.1 |
| 8,871,732 B2 | 10/2014 | Dina et al. |
| 8,889,181 B2 | 11/2014 | Kwon |
| 8,933,046 B2 | 1/2015 | Machuy et al. |
| 8,945,590 B2 | 2/2015 | Fairman et al. |
| 8,968,746 B2 | 3/2015 | Baumhof et al. |
| 9,066,978 B2 | 6/2015 | Ilyinskii et al. |
| 9,139,827 B2 | 9/2015 | Mirkin et al. |
| 9,216,155 B2 | 12/2015 | Thaxton et al. |
| 9,389,236 B2 | 7/2016 | Fandl et al. |
| 9,506,056 B2 | 11/2016 | Mirkin et al. |
| 9,532,948 B2 | 1/2017 | Mirkin et al. |
| 9,549,901 B2 | 1/2017 | Shi et al. |
| 9,617,541 B2 | 4/2017 | Mirkin et al. |
| 9,617,547 B2 | 4/2017 | Gemba |
| 9,693,957 B2 | 7/2017 | Lin et al. |
| 9,764,031 B2 | 9/2017 | Ilyinskii et al. |
| 9,844,562 B2 | 12/2017 | Mirkin et al. |
| 9,868,955 B2 | 1/2018 | Guiducci et al. |
| 9,889,209 B2 | 2/2018 | Mirkin et al. |
| 9,901,616 B2 | 2/2018 | Dhar et al. |
| 9,907,845 B2 | 3/2018 | Reed et al. |
| 9,999,673 B2 | 6/2018 | Rajeev et al. |
| 10,029,016 B2 | 7/2018 | Irvine et al. |
| 10,078,092 B2 | 9/2018 | Mutharasan et al. |
| 10,098,958 B2 | 10/2018 | Mirkin et al. |
| 10,144,933 B2 | 12/2018 | Gemba et al. |
| 10,182,988 B2 | 1/2019 | Mirkin et al. |
| 10,196,643 B2 | 2/2019 | Dina et al. |
| 10,208,310 B2 | 2/2019 | Mader et al. |
| 10,328,026 B2 | 6/2019 | Thaxton et al. |
| 10,370,656 B2 | 8/2019 | Mirkin et al. |
| 10,391,116 B2 | 8/2019 | Mirkin et al. |
| 10,398,784 B2 | 9/2019 | Mirkin et al. |
| 10,413,565 B2 | 9/2019 | Plebanek et al. |
| 10,434,064 B2 | 10/2019 | Radovic-Moreno et al. |
| 10,517,927 B2 | 12/2019 | Braddock et al. |
| 10,568,898 B2 | 2/2020 | Thaxton et al. |
| 10,704,043 B2 | 7/2020 | Daniel et al. |
| 10,760,080 B2 | 9/2020 | Mader et al. |
| 10,792,251 B2 | 10/2020 | Mirkin et al. |
| 10,837,018 B2 | 11/2020 | Radovic-Moreno et al. |
| 10,894,963 B2 | 1/2021 | Radovic-Moreno et al. |
| 11,123,294 B2 | 9/2021 | Radovic-Moreno et al. |
| 2002/0039568 A1 | 4/2002 | Moore et al. |
| 2002/0156033 A1 | 10/2002 | Bratzler et al. |
| 2002/0172711 A1 | 11/2002 | Martin et al. |
| 2002/0172953 A1 | 11/2002 | Mirkin et al. |
| 2002/0197269 A1 | 12/2002 | Lingnau et al. |
| 2003/0026782 A1 | 2/2003 | Krieg |
| 2003/0050261 A1 | 3/2003 | Krieg et al. |
| 2003/0091599 A1 | 5/2003 | Davis et al. |
| 2003/0104044 A1 | 6/2003 | Semple et al. |
| 2003/0129251 A1 | 7/2003 | Van Nest et al. |
| 2003/0133988 A1 | 7/2003 | Fearon et al. |
| 2003/0147966 A1 | 8/2003 | Franzen et al. |
| 2003/0170162 A1 | 9/2003 | Nayfeh et al. |
| 2004/0014956 A1 | 1/2004 | Woolf et al. |
| 2004/0023335 A1 | 2/2004 | Jing et al. |
| 2004/0023382 A1 | 2/2004 | Dean et al. |
| 2004/0053384 A1 | 3/2004 | Sligar et al. |
| 2004/0087534 A1 | 5/2004 | Krieg et al. |
| 2004/0092468 A1 | 5/2004 | Schwartz |
| 2004/0143112 A1 | 7/2004 | Krieg et al. |
| 2004/0158051 A1 | 8/2004 | Ozkan et al. |

(56) References Cited

U.S. PATENT DOCUMENTS

| | | |
|---|---|---|
| 2004/0170560 A1 | 9/2004 | Fossheim et al. |
| 2004/0171109 A1 | 9/2004 | Haudenschild et al. |
| 2004/0234500 A1 | 11/2004 | Moore et al. |
| 2004/0247680 A1 | 12/2004 | Farokhzad et al. |
| 2004/0266719 A1 | 12/2004 | McCluskie et al. |
| 2005/0009773 A1 | 1/2005 | Kandimalla et al. |
| 2005/0112578 A1* | 5/2005 | Matsuura ............... B82Y 30/00 435/6.12 |
| 2005/0130911 A1 | 6/2005 | Uhlmann et al. |
| 2005/0169888 A1 | 8/2005 | Hartmann et al. |
| 2005/0208572 A1 | 9/2005 | Shaughnessy |
| 2006/0003962 A1 | 1/2006 | Ahluwalia et al. |
| 2006/0014191 A1 | 1/2006 | Lao et al. |
| 2006/0014713 A1 | 1/2006 | Agrawal et al. |
| 2006/0019916 A1 | 1/2006 | Krieg et al. |
| 2006/0073572 A1 | 4/2006 | Huang et al. |
| 2006/0083713 A1 | 4/2006 | Glasebrook et al. |
| 2006/0083781 A1 | 4/2006 | Shastri et al. |
| 2006/0100151 A1 | 5/2006 | Troutt |
| 2006/0251623 A1 | 11/2006 | Bachmann et al. |
| 2006/0292174 A1 | 12/2006 | de los Rios et al. |
| 2007/0065868 A1 | 3/2007 | Jing |
| 2007/0066554 A1 | 3/2007 | Krieg et al. |
| 2007/0184068 A1 | 8/2007 | Renner et al. |
| 2007/0243196 A1 | 10/2007 | Bruck et al. |
| 2007/0280936 A1 | 12/2007 | Moore et al. |
| 2008/0181928 A1 | 7/2008 | Hakimi-Mehr et al. |
| 2008/0194463 A1 | 8/2008 | Weller et al. |
| 2008/0206265 A1 | 8/2008 | Kandimalla et al. |
| 2008/0213177 A1 | 9/2008 | Rademacher et al. |
| 2008/0274454 A1 | 11/2008 | Mirkin et al. |
| 2008/0306016 A1 | 12/2008 | Mirkin et al. |
| 2008/0311182 A1 | 12/2008 | Ferrari et al. |
| 2009/0018028 A1 | 1/2009 | Lindsay et al. |
| 2009/0053169 A1 | 2/2009 | Castillo et al. |
| 2009/0068737 A1 | 3/2009 | Yao et al. |
| 2009/0075884 A1 | 3/2009 | Jacobs et al. |
| 2009/0081157 A1 | 3/2009 | Kornbluth et al. |
| 2009/0191188 A1 | 7/2009 | Krieg et al. |
| 2009/0209629 A1 | 8/2009 | Mirkin et al. |
| 2009/0275735 A1 | 11/2009 | Golstein et al. |
| 2009/0286853 A1 | 11/2009 | Gryaznov et al. |
| 2009/0299045 A1 | 12/2009 | Richards et al. |
| 2009/0317802 A1 | 12/2009 | Bhatia et al. |
| 2009/0322327 A1 | 12/2009 | Gao |
| 2009/0324706 A1 | 12/2009 | Mirkin et al. |
| 2010/0003287 A1 | 1/2010 | Mills et al. |
| 2010/0136682 A1 | 6/2010 | Mirkin et al. |
| 2010/0143246 A1 | 6/2010 | Shi et al. |
| 2010/0144848 A1 | 6/2010 | Vogel et al. |
| 2010/0166842 A1 | 7/2010 | Lu et al. |
| 2010/0183634 A1 | 7/2010 | Luo et al. |
| 2010/0184844 A1 | 7/2010 | Mirkin et al. |
| 2010/0233270 A1 | 9/2010 | Mirkin et al. |
| 2010/0278840 A1 | 11/2010 | Mohler |
| 2011/0052697 A1 | 3/2011 | Farokhzad et al. |
| 2011/0111974 A1 | 5/2011 | Mirkin et al. |
| 2011/0201672 A1 | 8/2011 | Krieg et al. |
| 2011/0293700 A1 | 12/2011 | Bratzler et al. |
| 2011/0293701 A1 | 12/2011 | Bratzler et al. |
| 2011/0293723 A1 | 12/2011 | Bratzler et al. |
| 2011/0305734 A1 | 12/2011 | Edelson et al. |
| 2012/0082616 A1 | 4/2012 | Trawick et al. |
| 2012/0149843 A1 | 6/2012 | Chien et al. |
| 2012/0244230 A1 | 9/2012 | Mirkin et al. |
| 2012/0258126 A1 | 10/2012 | Scholler et al. |
| 2012/0301499 A1 | 11/2012 | Bachmann et al. |
| 2013/0028857 A1 | 1/2013 | Gao et al. |
| 2013/0034599 A1 | 2/2013 | Thaxton et al. |
| 2013/0071403 A1 | 3/2013 | Rolland et al. |
| 2013/0089614 A1 | 4/2013 | Zhang et al. |
| 2013/0095039 A1 | 4/2013 | Lu et al. |
| 2013/0101512 A1 | 4/2013 | Mirkin et al. |
| 2013/0123333 A1 | 5/2013 | Mirkin et al. |
| 2013/0149374 A1 | 6/2013 | Lee et al. |
| 2013/0178610 A1 | 7/2013 | Mirkin et al. |
| 2013/0252852 A1 | 9/2013 | Pfeiffer et al. |
| 2013/0315831 A1 | 11/2013 | Shi et al. |
| 2014/0005258 A1 | 1/2014 | Mirkin et al. |
| 2014/0037635 A1 | 2/2014 | Medlock et al. |
| 2014/0065425 A1 | 3/2014 | Bogdanov |
| 2014/0179770 A1* | 6/2014 | Zhang ..................... C12N 9/96 435/320.1 |
| 2014/0199379 A1 | 7/2014 | Tartour et al. |
| 2014/0294927 A1 | 10/2014 | Thaxton et al. |
| 2015/0086985 A1 | 3/2015 | Giljohann et al. |
| 2015/0118264 A1 | 4/2015 | Baumhof et al. |
| 2016/0101128 A1 | 4/2016 | Wang et al. |
| 2016/0108123 A1 | 4/2016 | Freeman et al. |
| 2016/0123964 A1 | 5/2016 | Tumeh et al. |
| 2016/0159905 A1 | 6/2016 | Abdiche et al. |
| 2016/0186178 A1 | 6/2016 | Radovic-Moreno et al. |
| 2016/0194642 A1 | 7/2016 | Gryaznov et al. |
| 2016/0310425 A1 | 10/2016 | Mirkin et al. |
| 2016/0339090 A1 | 11/2016 | Hacohen et al. |
| 2016/0375115 A1 | 12/2016 | Binder et al. |
| 2017/0044544 A1 | 2/2017 | Mirkin et al. |
| 2017/0157048 A1 | 6/2017 | Radovic-Moreno et al. |
| 2017/0175121 A1 | 6/2017 | Gryaznov |
| 2017/0232109 A1 | 8/2017 | Mirkin et al. |
| 2017/0240960 A1 | 8/2017 | Giljohann et al. |
| 2017/0274004 A1 | 9/2017 | Wang et al. |
| 2017/0306038 A1 | 10/2017 | Brogdon et al. |
| 2017/0306331 A1 | 10/2017 | Mader et al. |
| 2017/0326232 A1 | 11/2017 | Guiducci et al. |
| 2018/0000851 A1 | 1/2018 | Krieg |
| 2018/0042848 A1 | 2/2018 | Gryaznov et al. |
| 2018/0043023 A1 | 2/2018 | Ilyinskii et al. |
| 2018/0085350 A1 | 3/2018 | Avigan et al. |
| 2018/0085398 A1 | 3/2018 | Avigan et al. |
| 2018/0140691 A1 | 5/2018 | Takasu et al. |
| 2018/0214376 A1 | 8/2018 | Giljohann |
| 2018/0222982 A1 | 8/2018 | Dranoff et al. |
| 2018/0311176 A1 | 11/2018 | Ozsolak et al. |
| 2018/0318365 A1 | 11/2018 | Yeung et al. |
| 2018/0320184 A1 | 11/2018 | Radovic-Moreno et al. |
| 2018/0327741 A1 | 11/2018 | Daniel et al. |
| 2018/0344873 A1 | 12/2018 | Mirkin et al. |
| 2019/0030185 A1 | 1/2019 | Mirkin et al. |
| 2019/0083626 A1 | 3/2019 | Goldberg et al. |
| 2019/0142739 A1 | 5/2019 | Patel et al. |
| 2019/0153098 A1 | 5/2019 | Goldberg et al. |
| 2019/0211338 A1 | 7/2019 | Mader et al. |
| 2019/0225968 A1 | 7/2019 | Anderson et al. |
| 2019/0275166 A1 | 9/2019 | Mirkin et al. |
| 2020/0022913 A1 | 1/2020 | Mirkin et al. |
| 2020/0069587 A1 | 3/2020 | Radovic-Moreno et al. |
| 2020/0101156 A1 | 4/2020 | Mirkin et al. |
| 2020/0188521 A1 | 6/2020 | Kang et al. |
| 2020/0248183 A1 | 8/2020 | Nallagatla et al. |
| 2020/0255837 A9 | 8/2020 | Anderson et al. |
| 2020/0291394 A1 | 9/2020 | Mirkin et al. |
| 2020/0297867 A1 | 9/2020 | Kang et al. |
| 2020/0308579 A1 | 10/2020 | Kang |
| 2020/0339989 A1 | 10/2020 | Daniel et al. |
| 2020/0339996 A1 | 10/2020 | Mader et al. |
| 2020/0384104 A1 | 12/2020 | Mirkin et al. |
| 2021/0002640 A1 | 1/2021 | Kang et al. |
| 2021/0052497 A1 | 2/2021 | Mirkin et al. |
| 2021/0102211 A1 | 4/2021 | Radovic-Moreno et al. |
| 2021/0269806 A1 | 9/2021 | Anderson |

FOREIGN PATENT DOCUMENTS

| | | |
|---|---|---|
| CN | 1357042 A | 7/2002 |
| CN | 102036652 A | 4/2011 |
| CN | 102165061 A | 8/2011 |
| EP | 1 251 872 A1 | 10/2002 |
| EP | 1 255 837 A2 | 11/2002 |
| EP | 1 266 002 A2 | 12/2002 |
| EP | 1 326 974 B1 | 12/2006 |
| EP | 1 889 911 A2 | 2/2008 |
| EP | 0 959 897 B1 | 4/2009 |
| EP | 0 817 847 B2 | 9/2009 |

(56) References Cited

FOREIGN PATENT DOCUMENTS

| | | |
|---|---|---|
| EP | 1 015 488 B1 | 9/2009 |
| EP | 2162117 A2 | 3/2010 |
| EP | 2 366 406 A1 | 9/2011 |
| EP | 2399608 A1 | 12/2011 |
| EP | 1807094 B1 | 1/2012 |
| EP | 2451974 A2 | 5/2012 |
| EP | 2656858 A1 | 10/2013 |
| EP | 1 294 765 B1 | 11/2013 |
| EP | 3 112 468 A1 | 1/2017 |
| WO | WO 1992/021330 A1 | 12/1992 |
| WO | WO 1993/021528 A1 | 10/1993 |
| WO | WO 1994/001550 A1 | 1/1994 |
| WO | WO-9401550 A1 * | 1/1994 ............ C07H 21/00 |
| WO | WO 1996/029408 A1 | 9/1996 |
| WO | WO 1998/004740 A1 | 2/1998 |
| WO | WO 1998/018810 A1 | 5/1998 |
| WO | WO 1998/023284 A1 | 6/1998 |
| WO | WO 1999/027086 A1 | 6/1999 |
| WO | WO 1999/035267 A1 | 7/1999 |
| WO | WO 2000/013024 A1 | 3/2000 |
| WO | WO 2000/015759 A1 | 3/2000 |
| WO | WO 2000/020593 A1 | 4/2000 |
| WO | WO 2000/020645 A1 | 4/2000 |
| WO | WO 2000/029567 A1 | 5/2000 |
| WO | WO 2000/042188 A2 | 7/2000 |
| WO | WO 2000/055204 A1 | 9/2000 |
| WO | WO 2000/069463 A1 | 11/2000 |
| WO | WO 2001/000876 A1 | 1/2001 |
| WO | WO 2001/022990 A2 | 4/2001 |
| WO | WO 2001/057202 A2 | 8/2001 |
| WO | WO 2001/059120 A2 | 8/2001 |
| WO | WO 2001/064240 A2 | 9/2001 |
| WO | WO 2001/068859 A2 | 9/2001 |
| WO | WO 2002/058717 A2 | 8/2002 |
| WO | WO 2003/008539 A2 | 1/2003 |
| WO | WO 2002/038764 A3 | 7/2003 |
| WO | WO 2003/055980 A2 | 7/2003 |
| WO | WO 2002/102411 A3 | 9/2003 |
| WO | WO 2002/064739 A3 | 6/2004 |
| WO | WO 2004/047870 A1 | 6/2004 |
| WO | WO 2005/063201 A2 | 7/2005 |
| WO | WO 2005/063288 A1 | 7/2005 |
| WO | WO 2005/116226 A2 | 12/2005 |
| WO | WO 2006/015560 A1 | 2/2006 |
| WO | WO 2006/080946 A2 | 8/2006 |
| WO | WO 2006/088833 A2 | 8/2006 |
| WO | WO 2006/110350 A2 | 10/2006 |
| WO | WO 2006/138145 A1 | 12/2006 |
| WO | WO 2007/047455 A2 | 4/2007 |
| WO | WO 2007/055682 A2 | 5/2007 |
| WO | WO 2007/055704 A2 | 5/2007 |
| WO | WO 2007/060406 A1 | 5/2007 |
| WO | WO 2007/064857 A2 | 6/2007 |
| WO | WO 2007/089607 A2 | 8/2007 |
| WO | WO 2007/106683 A2 | 9/2007 |
| WO | WO 2007/122405 A1 | 11/2007 |
| WO | WO 2008/014979 A2 | 2/2008 |
| WO | WO 2008/042156 A1 | 4/2008 |
| WO | WO 2008/097328 A2 | 8/2008 |
| WO | WO 2008/127789 A2 | 10/2008 |
| WO | WO 2008/137762 A2 | 11/2008 |
| WO | WO 2008/141289 A1 | 11/2008 |
| WO | WO 2009/012786 A2 | 1/2009 |
| WO | WO 2009/026412 A1 | 2/2009 |
| WO | WO 2009/051451 A2 | 4/2009 |
| WO | WO 2009/061515 A1 | 5/2009 |
| WO | WO 2009/073984 A1 | 6/2009 |
| WO | WO 2009/105260 A2 | 8/2009 |
| WO | WO 2009/120887 A2 | 10/2009 |
| WO | WO 2009/131704 A2 | 10/2009 |
| WO | WO 2010/017152 A2 | 2/2010 |
| WO | WO 2010/017154 A2 | 2/2010 |
| WO | WO 2010/085959 A1 | 8/2010 |
| WO | WO 2010/091293 A1 | 8/2010 |
| WO | WO 2010/120420 A1 | 10/2010 |
| WO | WO 2010/148249 A1 | 12/2010 |
| WO | WO 2011/017456 A2 | 2/2011 |
| WO | WO 2011/017690 A2 | 2/2011 |
| WO | WO 2010/147387 A3 | 5/2011 |
| WO | WO 2011/053940 A2 | 5/2011 |
| WO | WO 2011/072133 A1 | 6/2011 |
| WO | WO 2011/079290 A1 | 6/2011 |
| WO | WO 2011/091065 A2 | 7/2011 |
| WO | WO 2011/113054 A2 | 9/2011 |
| WO | WO 2011/143608 A1 | 11/2011 |
| WO | WO 2012/055933 A1 | 5/2012 |
| WO | WO 2013/011368 A2 | 1/2013 |
| WO | WO 2013/012628 A2 | 1/2013 |
| WO | WO 2013/151771 A1 | 10/2013 |
| WO | WO 2013/177419 A2 | 11/2013 |
| WO | WO 2014/025795 A1 | 2/2014 |
| WO | WO 2014/123935 A1 | 8/2014 |
| WO | WO 2014/169264 A2 | 10/2014 |
| WO | WO 2014/175836 A1 | 10/2014 |
| WO | WO 2015/013673 A1 | 1/2015 |
| WO | WO 2015/013675 A1 | 1/2015 |
| WO | WO 2015/126502 A1 | 8/2015 |
| WO | WO 2015/153975 A1 | 10/2015 |
| WO | WO 2015/187966 A1 | 12/2015 |
| WO | WO 2015/195628 A2 | 12/2015 |
| WO | WO-2015187966 A1 * | 12/2015 ............ A61K 39/00 |
| WO | WO 2016/004168 A1 | 1/2016 |
| WO | WO 2016/057549 A1 | 4/2016 |
| WO | WO-2016057549 A1 * | 4/2016 ............ A61P 31/00 |
| WO | WO 2016/115320 A1 | 7/2016 |
| WO | WO 2016/134104 A1 | 8/2016 |
| WO | WO 2016/149323 A1 | 9/2016 |
| WO | WO 2016/149323 A2 | 9/2016 |
| WO | WO 2017/011662 A1 | 1/2017 |
| WO | WO 2017/035278 A1 | 3/2017 |
| WO | WO 2017/136467 A1 | 8/2017 |
| WO | WO 2017/161032 A1 | 9/2017 |
| WO | WO 2017/173334 A1 | 10/2017 |
| WO | WO 2017/181128 A1 | 10/2017 |
| WO | WO 2017/184427 A1 | 10/2017 |
| WO | WO 2017/193081 A1 | 11/2017 |
| WO | WO 2017/193084 A1 | 11/2017 |
| WO | WO 2017/193087 A1 | 11/2017 |
| WO | WO 2018/067302 A2 | 4/2018 |
| WO | WO 2018/152327 A2 | 8/2018 |
| WO | WO 2018/201090 A1 | 11/2018 |
| WO | WO 2018/209270 A1 | 11/2018 |
| WO | WO 2018/213585 A1 | 11/2018 |
| WO | WO 2019/118883 A2 | 6/2019 |
| WO | WO 2019/168558 A1 | 9/2019 |
| WO | WO 2019/169203 A1 | 9/2019 |
| WO | WO 2019/169328 A1 | 9/2019 |
| WO | WO 2019/246409 A1 | 12/2019 |
| WO | WO 2020/168005 A1 | 8/2020 |
| WO | WO 2020/219985 A1 | 10/2020 |
| WO | WO 2021/046254 A1 | 3/2021 |
| WO | WO 2021/202557 A1 | 10/2021 |

OTHER PUBLICATIONS

Supporting Information for Resham J. Banga, Natalia Chernyak, Suguna P. Narayan, SonBinh T. Nguyen, and Chad A. Mirkin. "Liposomal Spherical Nucleic Acids." Journal of the American Chemical Society, vol. 136, 2014, pp. S1-S13. (Year: 2014).*

Efstathios Karathanasis, Cissy M. Geigerman, Charles A. Parkos, Leslie Chan, Ravi V. Bellamkonda, and David L. Jaye. "Selective Targeting of Nanocarriers to Neutrophils and Monocytes." Annals of Biomedical Engineering, vol. 37, No. 10, Oct. 2009, pp. 1984-1992. (Year: 2009).*

Kazunori Matsuura, Kouzo Masumoto, Yuuko Igami, Tatsuro Fujioka, and Nobuo Kimizuka. "In Situ Observation of Spherical DNA Assembly in Water and the Controlled Release of Bound Dyes." Biomacromolecules, vol. 8, 2007, pp. 2726-2732. (Year: 2007).*

Kazunori Matsuura, Taro Yamashita, Yuuko Igami and Nobuo Kimizuka. "'Nucleo-nanocages': designed ternary oligodeoxyribonucleotides spontaneously form nanosized DNA cages." Chemical Communications, 2003, pp. 376-377. (Year: 2003).*

(56) References Cited

OTHER PUBLICATIONS

Neeshma Dave and Juewen Liu. "Programmable Assembly of DNA Functionalized Liposomes by DNA." ACS Nano, vol. 5, No. 2, 2011, pp. 1304-1312. (Year: 2011).*
Qing Ge et al. "Effects of chemical modification on the potency, serum stability, and immunostimulatory properties of short shRNAs." RNA, vol. 16, 2010, pp. 118-130. (Year: 2010).*
J.N. Israelachvili, S. Marcelja, and R.G. Horn. "Physical principles of membrane organization." Quarterly Reviews of Biophysics, vol. 13, No. 2, 1980, pp. 121-200. (Year: 1980).*
Matthew P. Thompson, Miao-Ping Chien, Ti-Hsuan Ku, Anthony M. Rush, and Nathan C. Gianneschi. "Smart Lipids for Programmable Nanomaterials." Nano Letters, vol. 10, 2010, pp. 2690-2693. (Year: 2010).*
Xin Ming, Brian Laing. "Bioconjugates for targeted delivery of therapeutic oligonucleotides." Advanced Drug Delivery Reviews, vol. 87, 2015, pp. 81-89. (Year: 2015).*
Yee-Hung M. Chan, Bettina van Lengerich, and Steven G. Boxer. "Lipid-anchored DNA mediates vesicle fusion as observed by lipid and content mixing." BioInterphases, vol. 3(2), Jun. 2008, pp. FA17-FA21. (Year: 2008).*
International Search Report and Written Opinion dated Aug. 1, 2018 for PCT/US2018/030021.
International Preliminary Report on Patentability dated Nov. 7, 2019 for International Application No. PCT/US2018/030021.
Agbasi-Porter et al., Transcription inhibition using oligonucleotide-modified gold nanoparticles, Bioconjugate Chem., 17(5):1178-83 (2006).
Akhter et al., Gold nanoparticles in theranostic oncology: current state-of-the-art. Expert Opin Drug Deliv. Oct. 2012;9(10):1225-43. Epub Aug. 16, 2012.
Ali et al., Vaccines Combined with Immune Checkpoint Antibodies Promote Cytotoxic T-cell Activity and Tumor Eradication. Cancer Immunol Res. Feb. 2016;4(2):95-100. doi: 10.1158/2326-6066.CIR-14-0126. Epub Dec. 15, 2015.
Asthana et al., Mannosylated chitosan nanoparticles for delivery of antisense oligonucleotides for macrophage targeting. Biomed Res Int. 2014;2014:526391. doi: 10.1155/2014/526391. Epub Jun. 26, 2014.
Aurasense Therapeutics, NIH grant. Topically-delivered Target Gene Suppression of Immune Activation in Psoriasis. David Giljohann. Accessed on Aug. 2, 2017 from http://grantome.com/grant/NIH/R41-AR066438-01. Accessible online on Feb. 21, 2016 as verified through Wayback Machine.
Ballas et al., Induction of NK activity in murine and human cells by CpG motifs in oligodeoxynucleotides and bacterial DNA. J Immunol. Sep. 1, 1996;157(5):1840-5.
Banchelli, M. et al., "Phospholipid Membranes Decorated by Cholesterol-Based Oligonucleotides as Soft Hybrid Nanostructures," J. Phys. Chem., 2008, 112 (35), 10942-10952.
Banga et al., Cross-linked miceller spherical nucleic acids from thermoresponsive templates, J. Am. Chem. Soc. 139:4278-81 (2017).
Banga et al., Liposomal spherical nucleic acids. J Am Chem Soc. Jul. 16, 2014;136(28):9866-9. doi: 10.1021/ja504845f. Epub Jul. 1, 2014.
Bhattarai et al., "Enhanced Gene and siRNA Delivery by Polycation-Modified Mesoporous Silica Nanoparticles Loaded with Chloroquine," Pharm. Res., 2010, 27, 2556-2568.
Bitounis et al., Optimizing Druggability through Liposomal Formulations: New Approaches to an Old Concept. ISRN Pharm. 2012;2012:738432. doi: 10.5402/2012/738432. Epub Feb. 9, 2012.
Bode et al. CpG DNA as a vaccine adjuvant. Expert Rev Vaccines. Apr. 2011;10(4):499-511. doi: 10.1586/erv.10.174.
Bonoiu et al., Nanotechnology approach for drug addiction therapy: gene ; silencing using delivery of gold nanorod-siRNA nanoplex in dopaminergic neurons. Proc Natl Acad Sci U S A. Apr. 7, 2009;106(14):5546-50. doi:; 10.1073/pnas.0901715106. Epub Mar. 23, 2009.

Bunge et al., Lipophilic oligonucleotides spontaneously insert into lipid membranes, bind complementary DNA strands, and sequester into lipid-disordered domains. Langmuir. Apr. 10, 2007;23(8):4455-64. Epub 2007 ar 17.
Chabaud et al., Enhancing effect of IL-17 on IL-1-induced IL-6 and leukemia inhibitory factor production by rheumatoid arthritis synoviocytes and its regulation by Th2 cytokines. J Immunol. Jul. 1, 1998;161(1):409-14.
Chen et al., Kinetics and thermodynamics of DNA hybridization on gold nanoparticles. Nucleic Acids Res. Jun. 2009;37(11):3756-65. doi: 10.1093/nar/gkp230. Epub Apr. 20, 2009.
Cheng et al., Interdigitated phospholipid/alkanethiol bilayers assembled on APTMS-supported gold colloid electrodes. Electroanalysis. 2004;16(1-2):127-31. doi:10.1002/elan.200302929.
Cheng et al., Tandem synthesis of core-shell brush copolymers and their transformation to peripherally cross-linked and hollowed nanostructures. J Am Chem Soc. May 31, 2006;128(21):6808-9. Published on web May 6, 2006.
Chinen et al., Spherical nucleic acid nanoparticle conjugates enhance G-quadruplex formation and increase serum protein interactions. Angew Chem Int Ed Engl. Jan. 7, 2015;54(2):527-31. doi: 10.1002/anie.201409211. Epub Nov. 13, 2014.
Cho et al., Targeted delivery of siRNA-generating DNA nanocassettes using multifunctional nanoparticles. Small. Jun. 10, 2013;9(11):1964-73. doi: 10.1002/smll.201201973. Epub Jan. 6, 2013.
Cho et al., Therapeutic nanoparticles for drug delivery in cancer. Clin Cancer Res. Mar. 1, 2008;14(5):1310-6. doi: 10.1158/1078-0432.CCR-07-1441.
Choi et al., Mechanism for the endocytosis of spherical nucleic acid nanoparticle conjugates, Proc. Natl. Acad. Sci. U.S.A. 2013;110:7625-7630.
Cload et al., Polyether tethered oligonucleotide probes. J. Am. Chem. Soc. 1991;113(16): 6324-6.
Cormode et al., "Nanocrystal Core High-Density Lipoproteins: A Multimodality Contrast Agent Platform," Nano Lett., 2008, 8 (11), 3715-3723.
Cutler et al., Polyvalent nucleic acid nanostructures. J Am Chem Soc. Jun. 22, 2011;133(24):9254-7. doi:10.1021/ja203375n. Epub Jun. 1, 2011.
Cutler et al., Polyvalent oligonucleotide iron oxide nanoparticle "click" conjugates. Nano Lett. Apr. 14, 2010;10(4):1477-80. doi:10.1021/nl100477m.
Cutler et al., Spherical nucleic acids. J Am Chem Soc. Jan. 25, 2012;134(3):1376-91. doi: 10.1021/ja209351u. Epub Jan. 9, 2012.
Daniel et al., Gold nanoparticles: assembly, supramolecular chemistry, quantum-size-related properties, and applications toward biology, catalysis, and nanotechnology. Chem Rev. Jan. 2004;104(1):293-346.
Dave et al., Programmable assembly of DNA-functionalized liposomes by DNA. ACS Nano. Feb. 22, 2011;5(2):1304-12. doi: 10.1021/nn1030093. Epub Jan. 4, 2011.
Demesmaeker et al., Antisense oligonucleotides. Acc. Chem. Res. 1995;28(9): 366-74.
Dhar et al., Polyvalent oligonucleotide gold nanoparticle conjugates as delivery vehicles for platinum (IV) warheads. J Am Chem Soc. Oct. 21, 2009; 131(41):14652-3. doi: 10.1021/ja907182.
Ding et al., A Crosslinked Nucleic Acid Nanogel for Effective siRNA Delivery and Antitumor Therapy. Angew Chem Int Ed Engl. Mar. 12, 2018;57(12):3064-3068. doi:10.1002/anie.201711242. Epub Feb. 22, 2018.
Ding et al., A statistical sampling algorithm for RNA secondary structure prediction. Nucleic Acids Res. Dec. 15, 2003;31(24):7280-301. doi: 10.1093/nar/gkg938.
Elbakry, A. et al., "Layer-by-Layer Assembled Gold Nanoparticles for siRNA Delivery," Nano Lett., 2009, 9 (5), 2059-2064.
Fan, H. et al., "Self-Assembly of Ordered, Robust, Three-Dimensional Gold Nanocrystal/Silica Arrays," Science, 2004, 403, 567-571.
Fattal et al., Biodegradable polyalkylcyanoacrylate nanoparticles for the delivery of oligonucleotides. J. Controlled Release. 1998;53:137-143.

(56) References Cited

OTHER PUBLICATIONS

Gao et al., Secondary structure effects on DNA hybridization kinetics: a solution versus surface comparison. Nucl. Acids Res. 2006;34: 3370-7.
Ghosh et al., Gold nanoparticles in delivery applications. Adv. Drug Deliv. Rev. 2008;60(11):1307-15.
Giljohann et al., Gene regulation with polyvalent siRNA-nanoparticle conjugates. J Am Chem Soc. Feb. 18, 2009; 131(6):2072-3.
Giljohann et al., Gold nanoparticles for biology and medicine. Angew Chem Int Ed Engl. Apr. 26, 2010;49(19):3280-94. doi: 10.1002/anie.200904359.
Giljohann et al., Oligonucleotide loading determines cellular uptake of DNA-modified gold nanoparticles. Nano Lett. Dec. 2007;7(12):3 818-21. Epub Nov. 13, 2007.
Gissot et al., Nucleoside, nucleotide and oligonucleotide based amphiphiles: a successful marriage of nucleic acids with lipids. Org. Biomol. Chem. 2008;6:1324-33.
Godard, G. et al., "Antisense Effects of Cholesterol-Oligodeoxynucleotide Conjugates Associated with Poly(alkylcyanoacrylate) Nanoparticles," Eur. J. Biochem., 1995, 232 (2), 404-410.
Grijalvo et al., Oligonucleotide delivery: a patent review (2010-2013). Expert Opin Ther Pat. Jul. 2014;24(7):801-19. doi:10.1517/13543776.2014.915944. Epub May 5, 2014.
Gryaznov, Oligonucleotide n3'-->p5' phosphoramidates and thiophosphoramidates as potential therapeutic agents. Chem Biodivers. Mar. 2010;7(3):477-93. doi: 10.1002/cbdv.200900187. Review.
Hames et al., Gene Probes 1 A Practical Approach, IRL Press, New York (1995).
Han et al., Drug and gene delivery using gold nanoparticles. NanoBiotechnology. Mar. 2007;3(1):40-5.
Hashmi et al., Gold catalysis. Angew Chem Int Ed Engl. Dec. 4, 2006;45(47):7896-936.
Hashmi, Gold-catalyzed organic reactions. Chem Rev. Jul. 2007;107(7):3180-211. Epub Jun. 20, 2007.
Hayashi, Ultrafine particles. J. Vac. Sci. Technol. 1987;5(4):1375-1384.
He et al., Phospholipid-stabilized Au-nanoparticles. Biomacromolecules. May-Jun. 2005;6(3):1224-5.
Hellstrom et al., Epitaxial growth of DNA-assembled nanoparticle superlattices on patterned substrates. Nano Lett. 2013;13(12):6084-90. doi: 10.1021/n14033654. Epub Nov. 20, 2013.
Hong et al., Directed Assembly of Nucleic Acid-Based Polymeric Nanoparticles from Molecular Tetravalent Cores, *J. Am. Chem. Soc.* 137:8184-91 (2015).
Huang et al., Sequence Multiplicity within Spherical Nucleic Acids. ACS Nano. Jan. 28, 2020;14(1):1084-1092. doi: 10.1021/acsnano.9b08750. Epub Jan. 9, 2020.
Hurst, S. et al., "Maximizing DNA Loading on a Range of Gold Nanoparticle Sizes," Anal. Chem., 2006, 78 (24), 8313-8318.
Jen et al., A nonviral transfection approach in vitro: the design of a gold nanoparticle vector joint with microelectromechanical systems. Langmuir, 2004;20(4): 1369-74.
Jensen et al., Spherical nucleic acid nanoparticle conjugates as an RNAi-based therapy for glioblastoma, Sci. Trans. Med., 5:209ra152 (2013).
Jin et al., What controls the melting properties of DNA-linked gold nanoparticle assemblies? J. Am. Chem. Soc. 2003;125: 1643.
Kachura et al., A CpG-Ficoll Nanoparticle Adjuvant for Anthrax Protective Antigen Enhances Immunogenicity and Provides Single-Immunization Protection against Inhaled Anthrax in Monkeys. J Immunol. Jan. 1, 2016;196(1):284-97. doi: 10.4049/jimmunol.1501903. Epub Nov. 25, 2015.
Karathanasis et al., Selective targeting of nanocarriers to neutrophils and monocytes. Ann Biomed Eng. Oct. 2009;37(10):1984-92. doi: 10.1007/s10439-009-9702-5. Epub Apr. 23, 2009.
Khmelinskaia et al., Effect of anchor positioning on binding and diffusion of elongated 3D DNA nanostructures on lipid membranes. J. Phys. D: Appl. Phys. Apr. 13, 2016;49(19):194001.

Kim et al., Cationic solid lipid nanoparticles reconstituted from low density lipoprotein components for delivery of siRNA. Mol Pharm. Jul.-Aug. 2008;5(4):622-31. doi: 10.1021/mp8000233. Epub May 8, 2008.
Kim, S. et al., "Systemic and Specific Delivery of Small Interfering RNAs to the Liver Mediated by Apolipoprotein A-I," Mol. Ther., 2007, 15 (6), 1145-1152.
Kolarova et al., Preparation of magnetic oligo (dT) particles. Biotechniques. 1996;20: 196-8.
Kong et al., Cationic lipid-coated gold nanoparticles as efficient and non-cytotoxic intracellular siRNA delivery vehicles. Pharm Res. Feb. 2012;29(2):362-74. doi: 10.1007/s11095-011-0554-y. Epub Aug. 13, 2011.
Krieg et al., CpG motifs in bacterial DNA trigger direct B-cell activation. Nature. Apr. 6, 1995;374(6522):546-9. doi: 10.1038/374546a0.
Krieg et al., Sequence motifs in adenoviral DNA block immune activation by stimulatory CpG motifs. Proc Natl Acad Sci U S A. Oct. 13, 1998;95(21):12631-6. doi: 10.1073/pnas.95.21.12631.
Kwoh et al., Stabilization of poly-L-lysine/DNA polyplexes for in vivo gene delivery to the liver. Biochim Biophys Acta. Feb. 16, 1999;1444(2):171-90.
Leander, D., "Mixed-Monolayer Gold Nanoparticles for Cancer Therapeutics," Nanoscape, 2010, 7 (1), 11-14.
Lee et al., A DNA-Gold Nanoparticle-Based Colormetric Competition Assay for the Detection of Cysteine. Nano Letter. 2008;8(2):529-533.
Lee et al., All-in-one target-cell-specific magnetic nanoparticles for simultaneous molecular imaging and siRNA delivery. Angew Chem Int Ed Engl. 2009;48(23):4174-9. doi:10.1002/anie.200805998.
Lee et al., Chip-based scanometric detection of mercuric ion using DNA-functionalized gold nanoparticles. Anal. Chem. 2008;80(17):6805-8.
Lee et al., Imageable antigen-presenting gold nanoparticle vaccines for effective cancer immunotherapy in vivo. Angew Chem Int Ed Engl. Aug. 27, 2012;51(35):8800-5. doi:10.1002/anie.201203193.
Leleux et al., Biophysical Attributes of CpG Presentation Control TLR9 Signaling to Differentially Polarize Systemic Immune Responses. Cell Rep. Jan. 17, 2017;18(3):700-710. doi: 10.1016/j.celrep.2016.12.073.
Lenert et al., Inhibitory oligonucleotides block the induction of AP-1 transcription factor by stimulatory CpG oligonucleotides in B cells. Antisense Nucleic Acid Drug Dev. 2003;13(3):143-50.
Lennox et al., Characterization of modified antisense oligonucleotides in Xenopus laevis embryos. Oligonucleotides. 2006 Spring;16(1):26-42.
Lewandowski et al., Topically delivered spherical nucleic acid nanoconjugates targeting TNF improve the psoriatic phenotype. J Invest Dermatol. 2015 135:S71. Abstract 413.
Lewandowski et al., Topically Delivered Tumor Necrosis Factor-?-Targeted Gene Regulation for Psoriasis. J Invest Dermatol. 2017;137(9):2027-2030. doi:10.1016/j.jid.2017.04.027.
Li et al., "Molecular spherical nucleic acids," PNAS pp. 1-5 (2018).
Li et al., Nanofabrication by DNA self-assembly. Materials Today. Elsevier Science. May 1, 2009;12(5)24-32.
Li et al., Nucleolin-targeting liposomes guided by aptamer AS1411 for the delivery of siRNA for the treatment of malignant melanomas. Biomaterials. Apr. 2014;35(12):3840-50. doi: 10.1016/j.biomaterials.2014.01.019. Epub Jan. 31, 2014.
Li et al., Reversible and Chemically Programmable Micelle Assembly with DNA Block-Copolymer Amphiphiles, Nano Lett. 2004;4:1055.
Li et al., Targeted delivery of antisense oligodeoxynucleotide and small interference RNA into lung cancer cells. Mol Pharm. Sep.-Oct. 2006;3(5):579-88. doi: 10.1021/mp060039w. Publication Date:Jul. 12, 2006.
Liu et al., "New poly(d-glucaramidoamine)s induce DNA nanoparticle formation and efficient gene delivery into mammalian cells," J. Am. Chem. Soc. 126:7422-7423 (2004).
Liu et al., DNA-based micelles: synthesis, micellar properties and size-dependent cell permeability, Chemistry. 2010;16:3791-7.
Liu et al., Membrane anchored immunostimulatory oligonucleotides for in vivo cell modification and localized immunotherapy.

(56) References Cited

OTHER PUBLICATIONS

Angew Chem Int Ed Engl. Jul. 25, 2011;50(31):7052-5. doi: 10.1002/anie.201101266. Epub Jun. 17, 2011.
Liu et al., Structure-based programming of lymph-node targeting in molecular vaccines. Nature. Mar. 27, 2014;507(7493):519-22. doi: 10.1038/nature12978.
Liu, J. et al., Silica Nanoparticle Supported Lipid Bilayers for Gene Delivery, Chem. Commun., 2009, 5100-5102.
Ljubimova et al., Nanoconjugate based on polymalic acid for tumor targeting. Chem Biol Interact. Jan. 30, 2008;171(2):195-203. Epub Feb. 8, 2007.
Luo et al., Locally instilled tumor necrosis factor a antisense oligonucleotide contributes to inhibition of TH 2-driven pulmonary fibrosis via induced CD4+ CD25+ Foxp3+ regulatory T cells. J Gene Med. Nov.-Dec. 2013; 15(11-12):441-52. doi: 10.1002/jgm.2750.
Lytton-Jean et al., A thermodynamic investigation into the binding properties of DNA functionalized gold nanoparticle probes and molecular fluorophore probes. J Am Chem Soc. Sep. 21, 2005;127(37):12754-5.
Major, M. et al., "Characterisation and Phase Behaviour of Phospholipid Bilayers Adsorbed on Spherical Polysaccharidic Nanoparticles," Biochimica et Biophysica Acta, 1997, 1327, 32-40.
Marinakos et al., Template Synthesis of One-Dimensional Au, Au-Poly(pyrrole), and Poly(pyrrole) Nanoparticle Arrays. Chem. Mater. 1998;10:1214-19.
Massich et al., Regulating immune response using polyvalent nucleic acid-gold nanoparticle conjugates. Mol Pharm. Nov.-Dec. 2009;6(6):1934-40.
Matijevic et al., Fine Particles Part II: Formation Mechanisms and Applications. MRS Bulletin pp. 16-47 (1990).
Matsunaga, T. et al., "Biomagnetic Nanoparticle Formation and Application," Supramolecular Science, 1998, 5 (3-4), 391-394.
Maye et al., A simple method for kinetic control of DNA-induced nanoparticle assembly. J. Am. Chem. Soc. 2006; 128: 14020-1.
McBain, S. et al., "Polyethyleneimine Functionalized Iron Oxide Nanoparticles as Agents for DNA Deliver and Transfection," J. Mater. Chem., 2007, 17, 2561-2565.
McKay et al., Characterization of a potent and specific class of antisense oligonucleotide inhibitor of human protein kinase C-alpha expression. J Biol Chem. Jan. 15, 1999;274(3):1715-22.
McMahon et al., Biomimetic high density lipoprotein nanoparticles for nucleic acid delivery. Nano Lett. Mar. 9, 2011;11(3):1208-14. doi: 10.1021/nl1041947. Epub Feb. 14, 2011.
Medintz et al., A reactive peptidic linker for self-assembling hybrid quantum dot-DNA bioconjugates. Nano Lett. Jun. 2007;7(6):1741-8. Epub May 26, 2007.
Miller et al., Antisense oligonucleotides: Strategies for delivery. PSTT. 1998;1(9): 377-86.
Ming et al., Albumin-based nanoconjugates for targeted delivery of ; therapeutic oligonucleotides. Biomaterials. Oct. 2013;34(32):7939-49. doi:; 10.1016/j.biomaterials.2013.06.066. Epub Jul. 19, 2013.
Miossec, Interleukin-17 in rheumatoid arthritis: if T cells were to contribute to inflammation and destruction through synergy. Arthritis Rheum. Mar. 2003;48(3):594-601. doi: 10.1002/art.10816. PMID: 12632409.
Mohamed et al., Effect of toll-like receptor 7 and 9 targeted therapy to prevent the development of hepatocellular carcinoma. Liver Int. Mar. 2015;35(3):1063-76. doi: 10.1111/liv.12626. Epub Jul. 30, 2014.
Monia et al., Nuclease resistance and antisense activity of modified oligonucleotides targeted to Ha-ras. J Biol Chem. Jun. 14, 1996;271(24):14533-40.
Moughton et al., Hollow nanostructures from self-assembled supramolecular metallo-triblock copolymers. Soft Matter. 2009;5(12):2361-70.
Mucic et al., Synthesis and characterization of DNA with ferrocenyl groups attached to their 5'-termini: electrochemical characterization of a redox-active nucleotide monolayer. Chem. Comm. 1996;555-7.

Nallagatla et al., Abstract 4706: Spherical nucleic acids targeting toll-like receptor 9 enhance antitumor activity in combination with anti-PD-1 antibody in mouse tumor models. Cancer Res. Jul. 1, 2017;22(13 Supplement):4706.
Nam et al., Nanoparticle-based bio-bar codes for the ultrasensitive detection of proteins. Science. Sep. 26, 2003;301(5641):1884-6.
Nemati et al., Using siRNA-based spherical nucleic acid nanoparticle conjugates for gene regulation in psoriasis. J Control Release. Dec. 28, 2017;268:259-268. doi: 10.1016/j.jconrel.2017.10.034. Epub Oct. 23, 2017.
Niemeyer, C. et al., "Bifunctional DNA-Gold Nanoparticle Conjugates as Building Blocks for the Self-Assembly of Cross-Linked Particle Layers," Biochemical and Biophysical Research Communications, 2003, 311 (4), 995-999.
Nikolov et al., Bias-dependent admittance in hybrid bilayer membranes. Langmuir. Aug. 15, 2006;22(17):7156-8.
Nuzzo et al., Spontaneously organized molecular assemblies. 3. Preparation and properties of solution adsorbed monolayers of organic disulfides on gold surfaces. J. Am. Chem. Soc. 1987;109:2358-68.
Pan et al., Dendrimer-Modified Magnetic Nanoparticles Enhance Efficiency of Gene Delivery System. Cancer Res. 2007;67:8156-8163.
Park et al., DNA-programmable nanoparticle cystrallization. Nature. 2008;451: 553-6.
Patel et al., Peptide antisense nanoparticles. Proc Natl Acad Sci U S A. Nov. 11, 2008;105(45):17222-6. doi: 10.1073/pnas.0801609105.
Patel et al., Scavenger receptors mediate cellular uptake of polyvalent oligonucleotide-functionalized gold nanoparticles, Bioconj. Chem., 21:2250 (2010).
Patil et al., "Evidence for Novel Interdigitated Bilayer Formation of Fatty Acids During Three-Dimensional Self-Assembly on Silver Colloidal Particles," J. Am. Chem. Soc., 1997, 119 (39), 9281-9282.
Patil et al., DNA-based therapeutics and DNA delivery systems: a comprehensive review. AAPS J., 2005;7(1): E61-77.
Patwa et al., Hybrid lipid oligonucleotide conjugates: synthesis, self-assemblies and biomedical applications. Chem Soc Rev. 2011;40:5844-54.
Paul, New Way to Kill Lymphoma without Chemotherapy uses Golden Nanoparticles. Feinberg School of Medicine: Northwestern University. Jan. 22, 2013. 4 pages. ww.feinberg.northwestern.edu/news/2013/01/lymphoma_nanoparticales.html.
Peter et al., Characterization of suppressive oligodeoxynucleotides that inhibit Toll-like receptor-9-mediated activation of innate immunity. Immunology. Jan. 2008;123(1):118-28. Epub Oct. 23, 2007.
Plant et al., Self-assembled phospholipid/alkanethiol biomimetic bilayers on gold. Langmuir. 1993;9:2764-7.
Pokholenko et al., Lipid oligonucleotide conjugates as responsive nanomaterials for drug delivery. J of Materials Chemistry B. 2013;5329-34.
Ponnappa et al., Inhibition of tumor necrosis factor alpha secretion and prevention of liver injury in ethanol-fed rats by antisense oligonucleotides. Biochem Pharmacol. Feb. 15, 2005;69(4):569-77. Epub Dec. 30, 2004.
Qin et al., Significantly improved analytical sensitivity of lateral flow immunoassays by using thermal contrast. Angew Chem Int Ed Engl. Apr. 27, 2012;51(18):4358-61. doi:10.1002/anie.201200997. Epub Mar. 23, 2012.
Radovic-Moreno et al., Immunomodulatory spherical nucleic acids. Proc Natl Acad Sci U S A. Mar. 31, 2015;112(13):3892-7. doi: 10.1073/pnas.1502850112. Epub Mar. 16, 2015.
Rana et al., Monolayer coated gold nanoparticles for delivery applications. Adv Drug Deliv Rev. Feb. 2012;64(2):200-16. doi: 10.1016/j.addr.2011.08.006. Epub Sep. 6, 2011.
Rojanasakul et al., Antisense inhibition of silica-induced tumor necrosis factor in alveolar macrophages. J Biol Chem. Feb. 14, 1997;272(7):3910-4.
Romanucci et al., Synthesis, biophysical characterization and anti-HIV activity of d(TG3AG) Quadruplexes bearing hydrophobic tails at the 5'-end. Bioorg Med Chem. Feb. 1, 2014;22(3):960-6. doi: 10.1016/j.bmc.2013.12.051. Epub Jan. 4, 2014.

(56) References Cited

OTHER PUBLICATIONS

Rosi et al., Oligonucleotide-modified gold nanoparticles for intracellular gene regulation. Science. May 19, 2006;312(5776):1027-30.
Rubenstein et al., Antisense oligonucleotide intralesional therapy for human PC-3 prostate tumors carried in athymic nude mice. J Surg Oncol. Jul. 1996;62(3):194-200. doi: 10.1002/(SICI)1096-9098(199607)62:3<194::AID-JSO9>3.0.CO;2-2.
Rush et al., Intracellular mRNA regulation with self-assembled locked nucleic acid polymer nanoparticles. J Am Chem Soc. May 28, 2014;136(21):7615-8. doi: 10.1021/ja503598z. Epub May 14, 2014.
Seferos et al., Polyvalent DNA nanoparticle conjugates stabilize nucleic acids. Nano Lett. Jan. 2009;9(1):308-11.
Shahzad et al., Targeted delivery of small interfering RNA using reconstituted high-density lipoprotein nanoparticles. Neoplasia. Apr. 2011;13(4):309-19.
Shukla et al., Development of streptavidin-based ; nanocomplex for siRNA delivery. Mol Pharm. Dec. 2, 2013;10(12):4534-45. doi:; 10.1021/mp400355q. Epub Oct. 25, 2013.
Sita et al., Dual bioluminescence and near-infrared fluorescence monitoring to evaluate spherical nucleic acid nanoconjugate activity in vivo. Proc Natl Acad Sci U S A. Apr. 18, 2017;114(16):4129-4134. doi: 10.1073/pnas.1702736114. Epub Apr. 3, 2017.
Song et al., Backbone-modified oligonucleotides for tuning the cellular uptake behaviour of spherical nucleic acids. Biomater Sci. Feb. 28, 2017;5(3):412-416. doi: 10.1039/c6bm00792a.
Storhoff et al., Sequence-Dependent Stability of DNA-Modified Gold Nanoparticles. Langmuir. 2002;18: 6666-6670.
Stunz et al., Inhibitory oligonucleotides specifically block effects of stimulatory CpG oligonucleotides in B cells. Eur J Immunol. May 2002;32(5):1212-22.
Tang et al., Probing hydroxyl radicals and their imaging in living cells by use of FAM-DNA-Au nanoparticles. Chemistry. Jan. 7, 2008;14(2):522-8.
Taton et al., Scanometric DNA array detection with nanoparticle probes. Science, 2000;289(5485):1757-60.
Thomas, "The Interaction of HgCl2 with Sodium Thymonucleate," J. Am. Chem. Soc., 76:6032-6034 (1954).
Thompson et al., Smart lipids for programmable nanomaterials. Nano Lett. Jul. 14, 2010;10(7):2690-3. doi: 10.1021/n1101640k.
Tiwari et al., Functionalized gold nanoparticles and their biomedical applications. Nanomaterials. 2011;1:31-63. doi: 10.3390/nano1010031.
Tondelli et al., "Highly efficient cellular uptake of c-myb antisense oligonucleotides through specifically desianed polymeric nanospheres," Nucl. Acids Res. 26:5425-5431 (1998).
Tripathy et al., High Density Lipoprotein Nanoparticles Deliver RNAi to Endothelial Cells to Inhibit Angiogenesis. Part Part Syst Charact. Nov. 1, 2014;31(11):1141-1150.
United States Securities and Exchange Commission Form 8-K Current Report, Date of Report (Date of earliest event reported): Sep. 26, 2017, Exicure, Inc. Dated: Oct. 2, 2017 by David Giljohann Accessed from the internet (Oct. 11, 2018) at https://www.sec.gov/Archives/edgar/data/1698530/000119312517301064/d461080d8k.htm.
Wagner et al., Gene inhibition using antisense oligodeoxynucleotides. Nature, 1994;372: 333-5.
Wei et al., Polyvalent immunostimulatory nanoagents with self-assembled CpG oligonucleotide-conjugated gold nanoparticles. Angew Chem Int Ed Engl. Jan. 27, 2012;51(5):1202-6. doi:10.1002/anie.201105187. Epub Dec. 15, 2011.
Wilson et al., pH-Responsive nanoparticle vaccines for dual-delivery of antigens and immunostimulatory oligonucleotides. ACS Nano. May 28, 2013;7(5):3912-25. doi: 10.1021/nn305466z. Epub Apr. 30, 2013.
Wilton et al. Antisense oligonucleotide-induced exon skipping across the human dystrophin gene transcript. Mol Ther. Jul. 2007;15(7):1288-96. Epub Feb. 6, 2007.
Wolfrum et al., Mechanisms and optimization of in vivo delivery of lipophilic siRNAs. Nat Biotechnol. Oct. 2007;25(10):1149-57. Epub Sep. 16, 2007.
Wu et al., DNA aptamer-micelle as an efficient detection/delivery vehicle toward cancer cells. Proc Natl Acad Sci U S A. Jan. 5, 2010;107(1):5-10. doi: 10.1073/pnas.0909611107. Epub Dec. 22, 2009.
Wu et al., Intracellular fate of spherical nucleic acid nanoparticle conjugates. J Am Chem Soc. May 28, 2014;136(21):7726-33. doi: 10.1021/ja503010a. Epub May 19, 2014.
Xiao et al., Mannosylated bioreducible nanoparticle-mediated macrophage-specific Tnf-? RNA interference for IBD therapy. Biomaterials. Oct. 2013;34(30):7471-82. doi: 10.1016/j.biomaterials.2013.06.008. Epub Jun. 29, 2013.
Xu et al., A gold-nanoparticle-based real-time colorimetric screening method for endonuclease activity and inhibition. Angew. Chem. Int. Ed. Engl., 2007;46(19):3468-70.
Xu et al., Homogeneous detection of nucleic acids based upon the light scattering properties of silver-coated nanoparticle probes. Anal. Chem., 2007;79(17):6650-4.
Xu et al., Thermodynamics of DNA hybridization on gold nanoparticles. J. Am. Chem. Soc., 2005;127(38): 13227-31.
Yamamoto et al., Unique palindromic sequences in synthetic oligonucleotides are required to induce IFN [correction of INF] and augment IFN-mediated [correction of INF] natural killer activity. J Immunol. Jun. 15, 1992;148(12):4072-6.
Yamane et al., On the complexing of desoxyribonucleic acid (DNA) by mercuric ion. J. Am. Chem. Soc., 1961;83:2599-2607.
Yang et al., Inhibition of a C-rich oligodeoxynucleotide on activation of immune cells in vitro and enhancement of antibody response in mice. Immunology. Dec. 2010;131(4):501-12. doi: 10.1111/j.1365-2567.2010.03322.x.
Yao et al. Herpesvirus Saimiri encodes a new cytokine, IL-17, which binds to a novel cytokine receptor. Immunity. Dec. 1995;3(6):811-21.
Yin et al., Supramolecular self-assembled nanoparticles mediate oral delivery of therapeutic TNF-? siRNA against systemic inflammation. Angew Chem Int Ed Engl. May 27, 2013;52(22):5757-61. doi: 10.1002/anie.201209991. Epub Apr. 22, 2013.
Zhang et al., "A general strategy for the DNA-mediated self-assembly of functional nanoparticles into heterogeneous systems," Nat Nanotechnol 8(11): 865-872 (2013).
Zhang et al., A general approach to DNA-programmable atom equivalents. Nat Mater. Aug. 2013;12(8):741-6. doi: 10.1038/nmat3647. Epub May 19, 2013.
Zhang et al., Informational liposomes: Complexes derived from cholesteryl-conjugated oligonucleotides and liposomes. Tetrahedron Letters. 1996. 37(35):6243-6.
Zhang et al., Nanopod formation through gold nanoparticle templated and catalyzed crosslinking of polymers bearing pendant propargyl ethers. J Am Chem Soc. Nov. 3, 2010;132(43):15151-3.
Zhang et al., Self-assembled monolayers of terminal alkynes on gold. J Am Chem Soc. Apr. 25, 2007;129(16):4876-7. Epub Mar. 31, 2007.
Zheng et al., A spherical nucleic acid platform based on self-assembled DNA biopolymer for high-performance cancer therapy. ACS Nano. Aug. 27, 2013;7(8):6545-54. doi: n402344v. Epub Jul. 23, 2013.
Zheng et al., Sterically controlled docking of gold nanoparticles on ferritin; surface by DNA hybridization. Nanotechnology. Jul. 8, 2011;22(27):275312. doi:; 10.1088/0957-4484/22/27/275312. Epub May 26, 2011.
Zheng et al., Topical delivery of siRNA-based spherical nucleic acid nanoparticle conjugates for gene regulation. Proc Natl Acad Sci U S A. Jul. 24, 2012;109(30):11975-80. doi: 10.1073/pnas.1118425109. Epub Jul. 6, 2012.
De Titta et al., Nanoparticle conjugation of CpG enhances adjuvancy for cellular immunity and memory recall at low dose. Proc Natl Acad Sci U S A. Dec. 3, 2013;110(49):19902-7. doi: 10.1073/pnas.1313152110. Epub Nov. 18, 2013.
Inoue, Oligonucleotide therapeutics: past, present and future. Drug Delivery System. Jan. 2016;31(1):10-23.

(56) References Cited

OTHER PUBLICATIONS

Radovic-Moreno et al., Immunomodulatory spherical nucleic acids. Proc Natl Acad Sci U S A PNAS. Mar. 31, 2015;112(13):3892-7. doi: 10.1073/pnas.1502850112. Epub Mar. 16, 2015.

Somiya et al., Potential of a non-cationic lioposomes-based delivery system for nucleic acid medicines. Drug Delivery System. Jan. 2016;31(1):35-43.

Zhang et al., Influence of anchoring ligands and particle size on the colloidal stability and in vivo biodistribution of polyethylene glycol-coated gold nanoparticles in tumor-xenografted mice. Biomaterials. Apr. 2009;30(10):1928-36. doi: 10.1016/j.biomaterials.2008.12.038. Epub Jan. 7, 2009. Author Manuscript, 22 pages.

Huang et al., CRISPR Spherical Nucleic Acids. J Am Chem Soc. Oct. 19, 2022;144(41):18756-18760. doi: 10.1021/jacs.2c07913. Epub Oct. 6, 2022.

Krieg et al., Induction of systemic TH1-like innate immunity in normal volunteers following subcutaneous but not intravenous administration of CPG 7909, a synthetic B-class CpG oligodeoxynucleotide TLR9 agonist. J Immunother. Nov.-Dec. 2004;27(6):460-71. doi: 10.1097/00002371-200411000-00006.

Kusmierz et al., Defining the Design Parameters for in Vivo Enzyme Delivery Through Protein Spherical Nucleic Acids. ACS Cent Sci. May 27, 2020;6(5):815-822. doi: 10.1021/acscentsci.0c00313. Epub Apr. 27, 2020.

\* cited by examiner

| Lane # | Compound # or Oligo No.# |
|---|---|
| 1 | D |
| 2 | Oligo 1 |
| 3 | F |
| 4 | Oligo 2 |

| Lane # | Compound or Oligo sequence # | Lane # | Compound or Oligo sequence # |
|---|---|---|---|
| 1 | H | 11 | L |
| 2 | Oligo 5 | 12 | Oligo 12 |
| 3 | J | 13 | S |
| 4 | Oligo 9 | 14 | Oligo 21 |
| 5 | I | 15 | T |
| 6 | Oligo 6 | 16 | Oligo 22 |
| 7 | N | 17 | R |
| 8 | Oligo 14 | 18 | Oligo 20 |
| 9 | Q | 19 | Oligo 35 |
| 10 | Oligo 18 | | |

SEQUENCE LISTING

```
<160> NUMBER OF SEQ ID NOS: 5

<210> SEQ ID NO 1
<211> LENGTH: 23
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(23)
<223> OTHER INFORMATION: Modified by phosphodiester linkage

<400> SEQUENCE: 1
tcgtcgtttt gtcgttttgt cgt                                             23

<210> SEQ ID NO 2
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(15)
<223> OTHER INFORMATION: Modified by phosphodiester linkage
```

```
<400> SEQUENCE: 2
tcgttcgtcg acgaa                                          15

<210> SEQ ID NO 3
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(6)
<223> OTHER INFORMATION: Methylated
<220> FEATURE:
<221> NAME/KEY: misc_feature
<222> LOCATION: (7)..(13)
<223> OTHER INFORMATION: Modified by phosphodiester linkage
<220> FEATURE:
<221> NAME/KEY: misc_feature
<222> LOCATION: (13)..(18)
<223> OTHER INFORMATION: Methylated

<400> SEQUENCE: 3
ugggagtaga caagguac                                       18

<210> SEQ ID NO 4
<211> LENGTH: 12
<212> TYPE: DNA
<213> ORGANISM: Artificial Sequence
<220> FEATURE:
<223> OTHER INFORMATION: Synthetic polynucleotide

<400> SEQUENCE: 4
cgacgttcgt cg                                             12

<210> SEQ ID NO 5
<211> LENGTH: 13
<212> TYPE: DNA
<213> ORGANISM: Artificial Sequence
<220> FEATURE:
<223> OTHER INFORMATION: Synthetic polynucleotide

<400> SEQUENCE: 5
cggcgccgtg ccg                                            13
```

SYNTHESIS OF SPHERICAL NUCLEIC ACIDS USING LIPOPHILIC MOIETIES

RELATED APPLICATIONS

This application is a national stage filing under 35 U.S.C. § 371 of international application number PCT/US2018/030021, filed Apr. 27, 2018, which was published under PCT Article 21(2) in English and claims the benefit under 35 U.S.C. § 119(e) of U.S. provisional application Ser. No. 62/492,062, filed Apr. 28, 2017, each of which is herein incorporated by reference in its entirety.

BACKGROUND OF INVENTION

Spherical Nucleic Acids (SNAs) are a novel class of therapeutic agents that consist of oligonucleotides densely packed and radially oriented around spherical liposomal nanoparticles. SNAs by virtue of their 3-dimensional architecture exhibit the ability to enter cells without the need for auxiliary delivery vehicles or transfection reagents, by engaging scavenger receptors and lipid rafts. Previously, hydrophobic mono-lipophilic moieties, such as cholesterol or tocopherol have been used, and conjugated to oligonucleotides for synthesizing SNAs.

When using single lipophilic moiety, especially cholesterol, oligonucleotides containing G-rich or self-complementary motifs pose a particular challenge. If an oligonucleotide sequence contains self-complementary or G-rich motifs, and is functionalized to the liposome surface using a single lipophilic moiety, such as cholesterol, the resulting SNAs form a cloudy solution, tend to self-aggregate, and eventually precipitate out of solution. These SNA formulations are difficult to filter because the aggregates clog the filter. Bulk synthesis and long term storage are also problematic because the precipitated SNAs may not have the same properties and aggregates may have poor activity or cause unexpected side effects.

SUMMARY OF INVENTION

Some aspects of the present disclosure include a nanostructure comprising a spherical nucleic acid (SNA) comprising a core, a lipid shell having an inner surface surrounding the core and an outer surface with a oligonucleotide functionalized to the outer surface of the nanostructure by a moiety comprised of two or more lipophilic groups. In some embodiments, the core is a hollow or a solid core. In other embodiments, the core is a liposomal core. In some embodiments, the lipid shell is comprised of one type of lipid. In another embodiment, the lipid is a phospholipid. In another embodiment, the phospholipid is 1,2-dioleoyl-sn-glycero-3-phophocholine (DOPC).

In some embodiments, the moiety comprised of two or more lipophilic groups is attached to the oligonucleotide through a linker. In another embodiment, the linker is a hexaethyleneglycol linker. In other embodiments, the oligonucleotide is a single stranded oligonucleotide. In another embodiment, the oligonucleotide is an immunostimulatory oligonucleotide. In another embodiment, the oligonucleotide contains a self-complementary motif. In another embodiment, the oligonucleotide contains a G-rich motif. In some embodiments, the immunostimulatory oligonucleotide stimulates a toll-like receptor (TLR). In another embodiment, the TLR is TLR9. In some embodiments, the oligonucleotide is an antisense oligonucleotide.

In some embodiments, the moiety comprised of the two or more lipophilic groups is a di-alkyl. In another embodiment, the moiety comprised of the two or more lipophilic groups is distearyl. In other embodiments, the moiety comprised of the two or more lipophilic groups is a tri-alkyl. In other embodiments, the moiety comprised of the two or more lipophilic groups is comprised by an alkyl chain. In another embodiment, the alkyl chain is comprised of at least 10 carbons. In another embodiment, the alkyl chain is comprised of at least 14 carbons.

In some embodiments, the nanostructure contains 26 to 7,000 oligonucleotides. In another embodiment, the nanostructure contains 26 to 500 oligonucleotides. In another embodiment, the nanostructure contains 26 to 80 oligonucleotides. In another embodiment, the nanostructure contains at least 40 oligonucleotides. In yet other embodiments, the nanostructure contains 26 to 5,000, 26 to 2,000, 26 to 1,000, 26 to 800, 25 to 500, 26 to 300, 26 to 200, 26 to 100, 50 to 5,000, 50 to 2,000, 50 to 1,000, 50 to 800, 50 to 500, 50 to 300, 50 to 200, 50 to 100, 100 to 5,000, 100 to 2,000, 100 to 1,000, 100 to 800, 100 to 500, 100 to 300, 100 to 200, or 100 to 150 oligonucleotides.

In some embodiments, the nanostructure moiety comprised of two or more lipophilic groups is more stable in solution than a nanostructure with a moiety comprised of one lipophilic group.

In some embodiments, the nanostructure has a diameter of about 10 nm to about 100 nm. In another embodiment, the nanostructure has a diameter of about 20 nm to about 50 nm. In another embodiment, the nanostructure has a diameter of about 27 nm to about 37 nm. In another embodiment, the nanostructure has a diameter of about 27 nm. In another embodiment, the nanostructure has a diameter of about 37 nm.

Some aspects of the present disclosure include a composition of discrete nanostructures, wherein each nanostructure comprises a spherical nucleic acid (SNA) comprising a core, a lipid shell having an inner surface surrounding the core and an outer surface with 26-7,000 oligonucleotides functionalized to the outer surface of the nanostructure, wherein the oligonucleotides contain a self-complementary motif. In some embodiments, each discrete nanostructure has a diameter of about 10 nm to about 100 nm. In another embodiment, each discrete nanostructure has a diameter of about 20 nm to about 50 nm. In yet other embodiments, the nanostructure contains 26 to 5,000, 26 to 2,000, 26 to 1,000, 26 to 800, 25 to 500, 26 to 300, 26 to 200, 26 to 100, 50 to 5,000, 50 to 2,000, 50 to 1,000, 50 to 800, 50 to 500, 50 to 300, 50 to 200, 50 to 100, 100 to 5,000, 100 to 2,000, 100 to 1,000, 100 to 800, 100 to 500, 100 to 300, 100 to 200, or 100 to 150 oligonucleotides.

In some embodiments, the oligonucleotides contain a G-rich motif. In another embodiment, the oligonucleotides are immunostimulatory oligonucleotides. In another embodiment, the immunostimulatory oligonucleotides stimulate a toll-like receptor 9 (TLR9). In other embodiments, the oligonucleotides are antisense oligonucleotides.

In some embodiments, the core is a hollow or a solid core. In some embodiments, the composition has a polydispersity (PDI) of 0.1-0.4. In some embodiments, each discrete nanostructure has a Z average diameter of 30-1,300.

A method for eliciting an immune response is provided according to other aspects of the invention. The method involves contacting a cell with the nanostructure described herein or a composition described herein. In some embodiments, the nanostructure induces cytokine secretion. In another embodiment, the nanostructure activates interferon alpha (IFNα). In some embodiments, the cell is a peripheral blood mononuclear cell.

A method for regulating gene expression is provided according to other aspects of the invention. The method involves contacting a cell with a nanostructure described herein to regulate gene expression.

A method for treating an immune disorder is provided according to other aspects of the invention. The method involves administering to a cell in a subject a nanostructure described herein to deliver an immunostimulatory oligonucleotide that promotes an immune response or to deliver an immunoinhibitory oligonucleotide that decreases or prevents an immune response to treat the immune disorder. In some embodiments, the subject is a mammal. In another embodiment, the subject is a human. In some embodiments, the nanostructure is in contact with the cell at a concentration of 1 nM to 100 µM. In another embodiment, the nanostructure is in contact with the cell at a concentration of 1 µM to 10 µM. In some embodiments, the nanostructure is in contact with the cell for 24 hours.

Kits comprising one or more sealed vials comprising an amount of any of the oligonucleotides and related nanostructure reagents of the present invention are also provided. The kit may optionally include instructions for generating and/or using nanostructures and compositions of the present invention in hard copy or computer readable form.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

In FIG. 4A, SNA 1_10, SNA 1_20, SNA 1_25, SNA 1_30, and SNA 1_50 were analyzed by SEC with PBS running buffer. SNA 1_50 shows elution of the unbound oligonucleotide (11-12 minutes) with SNA peak (6-7 minutes) indicating unbound oligonucleotide when SNAs are loaded with over 25 oligos per nanoparticle with Oligo 1. In FIG. 4B, SNA 18_50, SNA 18_60, SNA 18_70, SNA 18_80, SNA 18_90, and SNA 18_100 were analyzed by SEC with PBS running buffer. SNA 18_70 shows elution of the unbound oligonucleotide (9 minutes) with SNA peak (6-7 minutes) indicating unbound oligonucleotide when SNAs are loaded at over 60 oligos per nanoparticle with Oligo 32.

DETAILED DESCRIPTION

Figure 1:
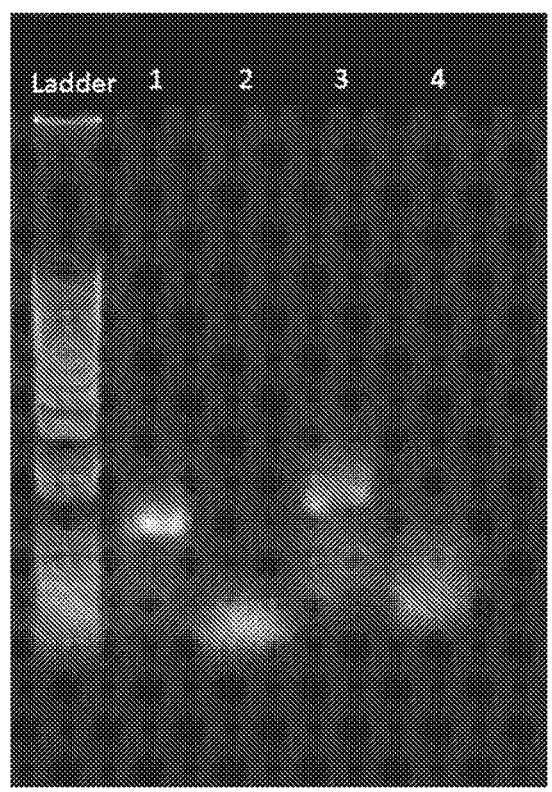
FIG. 1 agarose gel electrophoresis of SNA constructs and oligonucleotide-lipophilic moiety conjugates. Gel electrophoresis of SNA 1_30 (Lane 1), Oligo 1 (Lane 2), SNA 2 (Lane 3), and Oligo 2 (Lane 4), using 0.5% agarose stained with 0.5 µg/ml ethidium bromide is shown. SNA formation is observed for both SNA 1_30 and SNA 2, which have slower migration than their respective lipophilic moiety-conjugated oligonucleotides.

Spherical nucleic acids (SNAs) consist of densely packed, radially oriented nucleic acids. This architecture gives them unique properties, enabling cellular uptake of SNAs mediated via scavenger receptors. Cellular uptake of SNAs is fast and efficient and leads to endosomal accumulation.

Spherical nucleic acids (SNAs) are formed by organizing nucleic acids radially around a core. These structures exhibit the ability to enter cells without the need for auxiliary delivery vehicles or transfection reagents by engaging class A scavenger receptors (SR-A) and lipid rafts Once inside the cell, the nucleic acid components of traditional SNAs resist nuclease degradation, leading to longer intracellular lifetimes. Moreover, SNAs, due to their multi-functional chemical structures, have the ability to bind their targets in a multivalent fashion.

It has been discovered herein that SNA structures can be modified to significantly improve loading density with strategically designed lipophilic groups. SNAs have been developed according to the invention which have a densely packed oligonucleotide shell around a lipid structure. It was found that densely packing the oligonucleotides onto the surface can be achieved using a moiety comprised of two or more lipophilic groups, such as di-stearyl.

It has also been discovered herein that SNA formulation technology can be utilized to deliver self-aggregating oligonucleotides that have heretofore produced unacceptable aggregates that prevented their therapeutic use. SNAs composed of self-aggregating oligonucleotides have been developed according to the invention which incorporate oligonucleotides in a densely packed oligonucleotide shell. These unique molecules can be used to efficiently deliver any type of therapeutic or diagnostic self-aggregating oligonucleotide to a cell, and in particular to endosomes. A liposome or lipoplex can be functionalized into an SNA by inserting lipid-conjugated self-aggregating oligonucleotides onto the external surface. It has been discover that one method for densely packing the self-aggregating oligonucleotides onto the surface can be achieved using a moiety comprised of two or more lipophilic groups.

It is shown herein that when oligonucleotides containing self-complementary, e.g., G-rich motifs, are functionalized to liposome surface using two or more lipophilic groups, such as di-stearyl, the resulting SNAs do not aggregate or precipitate. This is particularly advantageous for large scale clinical and non-clinical preparations where SNAs need to be made in bulk, filter sterilized, and stored over extended periods. It is shown that the presence of multiple lipophilic groups enables higher density of oligonucleotides to be added to the liposome surface. The higher oligonucleotide density imparts stability to these SNAs, which are otherwise unstable, presumably by increasing electrostatic repulsion between SNAs, and promoting intra-SNA oligonucleotide interactions instead of inter-SNA oligonucleotide interactions. The resulting SNAs are active in immunostimulatory assays and can be used for other therapeutic indications such as gene regulation when functionalized with the appropriate antisense sequences.

Self-aggregating oligonucleotides in some embodiments have a self-complementary motif or are G-rich or GC rich. A self-complementary motif may be a region of 3, 4, 5, 6, 7, 8, 9, 10, 11, 12, 13, 14, or 15 or more nucleotides that base pair with a region of 3, 4, 5, 6, 7, 8, 9, 10, 11, 12, 13, 14, or 15 or more nucleotides in the same oligonucleotide or in other oligonucleotides within the SNAs. In some embodiments nucleotides are consecutive and in other embodiments there are 1 or more intervening nucleotides.

Compositions of SNA of the invention include discrete nanoparticles. The term "discrete" when used in the context of the nanoparticles refers to unaggregated nanoparticles. A composition of discrete nanoparticles includes at least 30% of the nanoparticles in the composition in an aggregated form. In some embodiments a composition of discrete nanoparticles includes at least 40, 45, 50, 55, 60, 65, 70, 75, 80, 85 90, 95, 96, 97, 98, or 99% or in some cases 100% of the nanoparticles in the composition in an unaggregated form.

A moiety comprised of two or more lipophilic groups as used herein is any compound having two lipophilic moieties capable of embedding in a lipid membrane. In some embodiments a moiety comprised of two or more lipophilic groups is a saturated or unsaturated, multi-alkyl chain lipophilic moiety, with carbon chains ranging from, for instance, C10 to C22, or di- and tri-alkyl chain lipophilic moiety. Di- and tri-alkyl chain lipophilic moiety-oligonucleotide conjugates can be synthesized by using symmetrical branching (doubler) and trebler reagents, respectively. As shown in the Examples below, various lipophilic moiety-oligonucleotide conjugates were studied for their ability to form SNAs with 20 nm DOPC liposomes. In contrast to the mono-alkyl lipophilic moiety-oligonucleotide conjugates that did not form SNAs, both di- and tri-alkyl chain lipophilic moiety-oligonucleotide conjugates formed SNAs.

Thus, the nanostructures of the invention are typically composed of lipid nanoparticles having a shell of oligonucleotides, which is formed by arranging oligonucleotides such that they point radially outwards from the core in a densely packed manner. A hydrophobic (e.g. lipophilic moiety) anchor group attached to either the 5'- or 3'-end of the oligonucleotide, depending on whether the oligonucleotides are arranged with the 5'- or 3'-end facing outward from the core preferably is used to embed the oligonucleotides in the lipid nanoparticle. The anchor acts to drive insertion into the lipid nanoparticle and to anchor the oligonucleotides to the lipids.

The density of self-aggregating oligonucleotides on the surface of the SNA of the invention is greater than the density of oligonucleotides positioned on the surface of traditional SNA which have oligonucleotides held on the surface using mono-lipophilic moieties such as cholesterol. Quite surprisingly, the improved density was shown to be associated with less inter-SNA aggregation. Compositions of unaggregated SNA are more stable. The density of the oligonucleotides can be described as a number of oligonucleotides per surface area.

The absolute number of oligonucleotides on the surface of a particle will depend on the size of the particle. For instance, on a 20 nm liposome an ideal number of oligonucleotides on the surface may be about 25-80, 26-80, 25-100, 26-100, 25-60, 26-60, 25-50, 26-50, 30-100, 30-80, 30-70, 30-60, 30-50, 30-40, 40-50, 40-60, or 50-60. Alternatively, on a 100 nm liposome core an ideal number of oligonucleotides on the surface may be about 5,000-6,000, 4,000-6,000, 4,500-6,000, or 5,500-6,000. In other embodiments the surface density of the multi-lipophilic moiety-self-aggregating oligonucleotide-SNAs of the invention is at least 2%, 3%, 4%, 5%, 6%, 7%, 8%, 9%, or 10% greater than the density of oligonucleotides positioned on the surface of traditional SNA which have oligonucleotides held on the surface using mono-lipophilic moieties such as cholesterol.

A surface density adequate to make the nanoparticles stable and not aggregate and the conditions necessary to obtain it for a desired combination of nanoparticles and oligonucleotides can be determined empirically.

In some aspects the SNAs may be used to deliver a therapeutic oligonucleotide to any tissue in which it is desirable to present the nucleic acid. For instance, it may be desirable to deliver the therapeutic oligonucleotide to the skin, a mucosal membrane, or an internal organ. The stable SNAs described herein are useful for delivering therapeutic oligonucleotides to these tissues for the treatment of disease or for diagnostic purposes.

The invention in some aspects relates to the delivery of an active agent that is a therapeutic nucleic acid. Therapeutic nucleic acids include inhibitory oligonucleotides and oligonucleotides that upregulate expression. In some embodiments the therapeutic nucleic acids specifically downregulate or upregulate the expression of a protein which is useful for being upregulated or downregulated in the eye and in particular in the cornea or retina or other related tissue. In other embodiments the therapeutic nucleic acids specifically downregulate or upregulate the expression of a protein which is useful for being upregulated or downregulated in other tissues. In some embodiments the nucleic acids are selected from the group consisting of a ribozyme, an interfering RNA (RNAi) molecule, a small inhibitory RNA (siRNA) molecule, a triple helix forming molecule, DNA, RNA, plasmids, antisense oligonucleotides, immunostimulatory oligonucleotides, immunoinhibitory oligonucleotides, mRNA, long ncRNA, and miRNA.

The terms "nucleic acid" and "oligonucleotide" are used interchangeably to mean multiple nucleotides (i.e., molecules comprising a sugar (e.g., ribose or deoxyribose) linked to a phosphate group and to an exchangeable organic base, which is either a substituted pyrimidine (e.g., cytosine (C), thymine (T) or uracil (U)) or a substituted purine (e.g., adenine (A) or guanine (G)). As used herein, the terms "nucleic acid" and "oligonucleotide" refer to oligoribonucleotides as well as oligodeoxyribonucleotides. The terms "nucleic acid" and "oligonucleotide" shall also include polynucleosides (i.e., a polynucleotide minus the phosphate) and any other organic base containing polymer. Nucleic acid molecules are preferably synthetic (e.g., produced by nucleic acid synthesis). The oligonucleotides may be any size useful for producing antisense effects. In some embodiments they are 18-23 nucleotides in length. In other embodiments the antisense oligonucleotide is 18 nucleotides in length.

The terms "nucleic acid" and "oligonucleotide" may also encompass nucleic acids or oligonucleotides with substitutions or modifications, such as in the bases and/or sugars. For example, they include nucleic acids having backbone sugars that are covalently attached to low molecular weight organic groups other than a hydroxyl group at the 2' position and other than a phosphate group or hydroxy group at the 5' position. Thus modified nucleic acids may include a 2'-O-alkylated ribose group. In addition, modified nucleic acids may include sugars such as arabinose or 2'-fluoroarabinose instead of ribose. Thus the nucleic acids may be heterogeneous in backbone composition thereby containing any possible combination of polymer units linked together such as peptide-nucleic acids (which have an amino acid backbone with nucleic acid bases). Other examples are described in more detail below.

The oligonucleotides may be DNA, RNA, PNA, LNA, ENA or hybrids including any chemical or natural modification thereof. Chemical and natural modifications are well known in the art. Such modifications include, for example, modifications designed to increase binding to a target strand (i.e., increase their melting temperatures), to assist in identification of the oligonucleotide or an oligonucleotide-target complex, to increase cell penetration, to stabilize against nucleases and other enzymes that degrade or interfere with the structure or activity of the oligonucleotides, to provide a mode of disruption (a terminating event) once sequence-specifically bound to a target, and to improve the pharmacokinetic properties of the oligonucleotide.

Modifications include, but are not limited to, for example, (a) end modifications, e.g., 5' end modifications (phosphorylation dephosphorylation, conjugation, inverted linkages, etc.), 3' end modifications (conjugation, DNA nucleotides, inverted linkages, etc.), (b) base modifications, e.g., replacement with modified bases, stabilizing bases, destabilizing bases, or bases that base pair with an expanded repertoire of partners, or conjugated bases, (c) sugar modifications (e.g., at the 2' position or 4' position) or replacement of the sugar, as well as (d) internucleoside linkage modifications, including modification or replacement of the phosphodiester linkages. To the extent that such modifications interfere with translation (i.e., results in a reduction of 50%, 60%, 70%, 80%, or 90% or more in translation relative to the lack of the modification—e.g., in an in vitro translation assay), the modification may not be optimal for the methods and compositions described herein.

Non-limiting examples of modified internucleoside linkages include phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Modified internucleoside linkages that do not include a phosphorus atom therein have internucleoside linkages that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Substituted sugar moieties include, but are not limited to one of the following at the 2' position: H (deoxyribose); OH (ribose); F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl.

A chemically or naturally modified oligonucleotide may include, for example, at least one nucleotide modified at the 2' position of the sugar, most preferably a 2'-O-alkyl, 2'-O-alkyl-O-alkyl or 2'-fluoro-modified nucleotide or an end cap. In other embodiments, RNA modifications include 2'-fluoro, 2'-amino and 2' O-methyl modifications on the ribose of pyrimidines, abasic residues or an inverted base at the 3' end of the RNA.

The oligonucleotides useful according to the invention may include a single modified nucleoside. In other embodiments the oligonucleotide may include at least two modified nucleosides, at least 3, at least 4, at least 5, at least 6, at least 7, at least 8, at least 9, at least 10, at least 15, at least 20 or more nucleosides, up to the entire length of the oligonucleotide.

Nucleosides or nucleobases include the natural purine bases adenine (A) and guanine (G), and the pyrimidine bases thymine (T), cytosine (C) and uracil (U). Modified nucleosides include other synthetic and natural nucleobases such as inosine, xanthine, hypoxanthine, nubularine, isoguanisine, tubercidine, 2-(halo)adenine, 2-(alkyl)adenine, 2-(propyl) adenine, 2 (amino)adenine, 2-(aminoalkyl)adenine, 2 (aminopropyl)adenine, 2 (methylthio) N6 (isopentenyl)adenine, 6 (alkyl)adenine, 6 (methyl)adenine, 7 (deaza)adenine, 8 (alkenyl)adenine, 8-(alkyl)adenine, 8 (alkynyl)adenine, 8 (amino)adenine, 8-(halo)adenine, 8-(hydroxyl)adenine, 8 (thioalkyl) adenine, 8-(thiol)adenine, N6-(isopentyl)adenine, N6 (methyl)adenine, N6, N6 (dimethyl)adenine, 2-(alkyl)guanine, 2 (propyl)guanine, 6-(alkyl)guanine, 6 (methyl)guanine, 7 (alkyl)guanine, 7 (methyl)guanine, 7 (deaza)guanine, 8 (alkyl)guanine, 8-(alkenyl)guanine, 8 (alkynyl)guanine, 8-(amino)guanine, 8 (halo)guanine, 8-(hydroxyl)guanine, 8 (thioalkyl)guanine, 8-(thiol)guanine, N (methyl)guanine, 2-(thio)cytosine, 3 (deaza) 5 (aza) cytosine, 3-(alkyl)cytosine, 3 (methyl)cytosine, 5-(alkyl) cytosine, 5-(alkynyl)cytosine, 5 (halo)cytosine, 5 (methyl) cytosine, 5 (propynyl)cytosine, 5 (propynyl)cytosine, 5 (trifluoromethyl)cytosine, 6-(azo)cytosine, N4 (acetyl)cytosine, 3 (3 amino-3 carboxypropyl)uracil, 2-(thio)uracil, 5 (methyl) 2 (thio)uracil, 5 (methylaminomethyl)-2 (thio)uracil, 4-(thio)uracil, 5 (methyl) 4 (thio)uracil, 5 (methylaminomethyl)-4 (thio)uracil, 5 (methyl) 2,4 (dithio)uracil, 5

(methylaminomethyl)-2,4 (dithio)uracil, 5 (2-aminopropyl) uracil, 5-(alkyl)uracil, 5-(alkynyl)uracil, 5-(allylamino)uracil, 5 (aminoallyl)uracil, 5 (aminoalkyl)uracil, 5 (guanidiniumalkyl)uracil, 5 (1,3-diazole-1-alkyl)uracil, 5-(cyanoalkyl) uracil, 5-(dialkylaminoalkyl)uracil, 5 (dimethylaminoalkyl) uracil, 5-(halo)uracil, 5-(methoxy)uracil, uracil-5 oxyacetic acid, 5 (methoxycarbonylmethyl)-2-(thio)uracil, 5 (methoxycarbonyl-methyl)uracil, 5 (propynyl)uracil, 5 (propynyl)uracil, 5 (trifluoromethyl)uracil, 6 (azo)uracil, dihydrouracil, N3 (methyl)uracil, 5-uracil (i.e., pseudouracil), 2 (thio)pseudouracil, 4 (thio)pseudouracil, 2,4-(dithio)psuedouracil, 5-(alkyl)pseudouracil, 5-(methyl)pseudouracil, 5-(alkyl)-2-(thio)pseudouracil, 5-(methyl)-2-(thio)pseudouracil, 5-(alkyl)-4 (thio)pseudouracil, 5-(methyl)-4 (thio) pseudouracil, 5-(alkyl)-2,4 (dithio)pseudouracil, 5-(methyl)-2,4 (dithio)pseudouracil, 1 substituted pseudouracil, 1 substituted 2(thio)-pseudouracil, 1 substituted 4 (thio)pseudouracil, 1 substituted 2,4-(dithio)pseudouracil, 1 (aminocarbonylethylenyl)-pseudouracil, 1 (aminocarbonylethylenyl)-2(thio)-pseudouracil, 1 (aminocarbonylethylenyl)-4 (thio)pseudouracil, 1 aminocarbonylethylenyl)-2,4-(dithio)pseudouracil, 1 (arninoalkylarninocarbonylethylenyl)-pseudouracil, 1 (arninoalkylarnino-carbonylethylenyl)-2(thio)-pseudouracil, 1(arninoalkylarninocarbonylethylenyl)-4 (thio)pseudouracil, 1 (arninoalkylarninocarbonyl-ethylenyl)-2,4-(dithio)pseudouracil, 1,3-(diaza)-2-(oxo)-phenoxazin-1-yl, 1-(aza)-2-(thio)-3-(aza)-phenoxazin-1-yl, 1,3-(diaza)-2-(oxo)-phenthiazin-1-yl, 1-(aza)-2-(thio)-3-(aza)-phenthiazin-1-yl, 7-substituted 1,3-(diaza)-2-(oxo)-phenoxazin-1-yl, 7-substituted 1-(aza)-2-(thio)-3-(aza)-phenoxazin-1-yl, 7-substituted 1,3-(diaza)-2-(oxo)-phenthiazin-1-yl, 7-substituted 1-(aza)-2-(thio)-3-(aza)-phenthiazin-1-yl, 7-(arninoalkylhydroxy)-1,3-(diaza)-2-(oxo)-phenoxazin-1-yl, 7-(arninoalkylhydroxy)-1-(aza)-2-(thio)-3-(aza)-phenoxazin-1-yl, 7-(aminoalkylhydroxy)-1,3-(diaza)-2-(oxo)-phenthiazin-1-yl, 7-(arninoalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(guanidiniumalkylhydroxy)-1-(aza)-2-(thio)-3-(aza)-phenoxazin-1-yl, 7-(guanidiniumalkyl-hydroxy)-1,3-(diaza)-2-(oxo)-phenthiazin-1-yl, 7-(guanidiniumalkylhydroxy)-1-(aza)-2-(thio)-3-(aza)-phenthiazin-1-yl, 1,3,5-(triaza)-2,6-(dioxa)-naphthalene, inosine, xanthine, hypoxanthine, nubularine, tubercidine, isoguanisine, inosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, 3-(methyl)isocarbostyrilyl, 5-(methyl)isocarbostyrilyl, 3-(methyl)-7-(propynyl)isocarbostyrilyl, 7-(aza)indolyl, 6-(methyl)-7-(aza)indolyl, imidizopyridinyl, 9-(methyl)-imidizopyridinyl, pyrrolopyrizinyl, isocarbostyrilyl, 7-(propynyl)isocarbostyrilyl, propynyl-7-(aza)indolyl, 2,4,5-(trimethyl)phenyl, 4-(methyl)indolyl, 4,6-(dimethyl)indolyl, phenyl, napthalenyl, anthracenyl, phenanthracenyl, pyrenyl, stilbenyl, tetracenyl, pentacenyl, diiluorotolyl, 4-(iluoro)-6-(methyl)benzimidazole, 4-(methyl)benzimidazole, 6-(azo) thymine, 2-pyridinone, 5 nitroindole, 3 nitropyrrole, 6-(aza) pyrimidine, 2 (amino)purine, 2,6-(diamino) purine, 5 substituted pyrimidines, N2-substituted purines, N6-substituted purines, 06-substituted purines, substituted 1,2,4-triazoles, pyrrolo-pyrimidin-2-on-3-yl, 6-phenyl-pyrrolo-pyrimidin-2-on-3-yl, para-substituted-6-phenyl-pyrrolo-pyrimidin-2-on-3-yl, ortho-substituted-6-phenyl-pyrrolo-pyrimidin-2-on-3-yl, bis-ortho-substituted-6-phenyl-pyrrolo-pyrimidin-2-on-3-yl, para-(aminoalkylhydroxy)-6-phenyl-pyrrolo-pyrimidin-2-on-3-yl, ortho-(aminoalkyl-hydroxy)-6-phenyl-pyrrolo-pyrimidin-2-on-3-yl, bis-ortho-(aminoalkylhydroxy)-6-phenyl-pyrrolo-pyrimidin-2-on-3-yl, pyridopyrimidin-3-yl, 2-oxo-7-amino-pyridopyrimidin-3-yl, 2-oxo-pyridopyrimidine-3-yl, or any O-alkylated or N-alkylated derivatives thereof.

The oligonucleotides of the invention may be chimeric oligonucleotides. Chimeric compounds of the invention may be formed as composite structures of two or more oligonucleotides, modified oligonucleotides, oligonucleotides and/or oligonucleotide mimetics as described above. Such compounds have also been referred to in the art as hybrids or gapmers. In particular a gapmer is an oligonucleotide that has at least three discrete portions, two of which are similar i.e. include one or more backbone modifications, and surround a region that is distinct, i.e., does not include backbone modifications.

In some embodiments, the backbone of the oligonucleotide is modified. In some embodiments, the backbone of the oligonucleotide has a phosphorothioate modification. The backbone of the oligonucleotide may have other modifications apparent to one of ordinary skill in the art.

Aspects of the invention relate to delivery of SNAs to a subject for therapeutic and/or diagnostic use. The SNAs may be administered alone or in any appropriate pharmaceutical carrier, such as a liquid, for example saline, or a powder, for administration in vivo. They can also be co-delivered with larger carrier particles or within administration devices. The SNAs may be formulated. The formulations of the invention can be administered in pharmaceutically acceptable solutions, which may routinely contain pharmaceutically acceptable concentrations of salt, buffering agents, preservatives, compatible carriers, adjuvants, and optionally other therapeutic ingredients. In some embodiments, SNAs associated with the invention are mixed with a substance such as a lotion (for example, aquaphor) and are administered to the skin of a subject, whereby the SNAs are delivered through the skin of the subject. It should be appreciated that any method of delivery of nanoparticles known in the art may be compatible with aspects of the invention.

For use in therapy, an effective amount of the SNAs can be administered to a subject by any mode that delivers the SNAs to the desired cell. Administering pharmaceutical compositions may be accomplished by any means known to the skilled artisan. Routes of administration include but are not limited to oral, parenteral, intramuscular, intravenous, subcutaneous, mucosal, intranasal, sublingual, intratracheal, inhalation, ocular, vaginal, dermal, rectal, and by direct injection.

In some embodiments the oligonucleotide is a G-rich oligonucleotide. The G-rich nucleic acids may have a sequence that includes at least 50% G's. In some embodiment the G-rich nucleic acids have a sequence that includes at least 60%, 70%, 80% or 90% G's. The G-rich nucleic acids may also have one or multiple G repeats. For instance, a G-rich nucleic acid may have a stretch of at least 4 G's. In other embodiments the G-rich nucleic acid may have one or more stretches of 3 G's. In yet other embodiments the G-rich nucleic acid may have multiple G dimers (e.g., 2, 3, 4, 5, or 6 dimers) separated by one or more other nucleotides.

The oligonuceltide of the SNA in some embodiments is comprised of densely packed, radially oriented nucleic acids which stimulate an immune response, and in particular stimulate the toll-like receptors (TLR) such as TLR9. In some embodiments the SNA is an agonist of a TLR (TLR agonist). A TLR agonist, as used herein is a nucleic acid molecule that interacts with and stimulates the activity of a TLR. The SNA, in some embodiments, is a TLR-9 targeted Immunostimulatory Sperical Nucleic Acid.

Toll-like receptors (TLRs) are a family of highly conserved polypeptides that play a critical role in innate immunity in mammals. At least ten family members, designated TLR1-TLR10, have been identified. The cytoplasmic domains of the various TLRs are characterized by a Toll-interleukin 1 (IL-1) receptor (TIR) domain. Medzhitov R et al. (1998) Mol Cell 2:253-8. Recognition of microbial invasion by TLRs triggers activation of a signaling cascade that is evolutionarily conserved in Drosophila and mammals. The TIR domain-containing adaptor protein MyD88 has been reported to associate with TLRs and to recruit IL-1 receptor-associated kinase (IRAK) and tumor necrosis factor (TNF) receptor-associated factor 6 (TRAF6) to the TLRs. The MyD88-dependent signaling pathway is believed to lead to activation of NF-κB transcription factors and c-Jun NH2 terminal kinase (Jnk) mitogen-activated protein kinases (MAPKs), critical steps in immune activation and production of inflammatory cytokines. For a review, see Aderem A et al. (2000) Nature 406:782-87.

TLRs are believed to be differentially expressed in various tissues and on various types of immune cells. For example, human TLR7 has been reported to be expressed in placenta, lung, spleen, lymph nodes, tonsil and on plasmacytoid precursor dendritic cells (pDCs). Chuang T-H et al. (2000) Eur Cytokine Netw 11:372-8); Kadowaki N et al. (2001) J Exp Med 194:863-9. Human TLR8 has been reported to be expressed in lung, peripheral blood leukocytes (PBL), placenta, spleen, lymph nodes, and on monocytes. Kadowaki N et al. (2001) J Exp Med 194:863-9; Chuang T-H et al. (2000) Eur Cytokine Netw 11:372-8. Human TLR9 is reportedly expressed in spleen, lymph nodes, bone marrow, PBL, and on pDCs, and B cells. Kadowaki N et al. (2001) J Exp Med 194:863-9; Bauer S et al. (2001) Proc Natl Acad Sci USA 98:9237-42; Chuang T-H et al. (2000) Eur Cytokine Netw 11:372-8.

Nucleotide and amino acid sequences of human and murine TLR9 are known. See, for example, GenBank Accession Nos. NM 017442, AF259262, AB045180, AF245704, AB045181, AF348140, AF314224, NM 031178; and NP 059138, AAF72189, BAB19259, AAF78037, BAB19260, AAK29625, AAK28488, and NP 112455, the contents of all of which are incorporated herein by reference. Human TLR9 is reported to exist in at least two isoforms, one 1032 amino acids long and the other 1055 amino acids. Murine TLR9 is 1032 amino acids long. TLR9 polypeptides include an extracellular domain having a leucine-rich repeat region, a transmembrane domain, and an intracellular domain that includes a TIR domain.

As used herein, the term "TLR9 signaling" refers to any aspect of intracellular signaling associated with signaling through a TLR9. As used herein, the term "TLR9-mediated immune response" refers to the immune response that is associated with TLR9 signaling. A TLR9-mediated immune response is a response associated with TLR9 signaling. This response is further characterized at least by the production/secretion of IFN-γ and IL-12, albeit at levels lower than are achieved via a TLR8-mediated immune response.

The term "TLR9 agonist" refers to any agent that is capable of increasing TLR9 signaling (i.e., an agonist of TLR9). TLR9 agonists specifically include, without limitation, immunostimulatory oligonucleotides, and in particular CpG immunostimulatory oligonucleotides.

An "immunostimulatory oligonucleotide" as used herein is any nucleic acid (DNA or RNA) containing an immunostimulatory motif or backbone that is capable of inducing an immune response. An induction of an immune response refers to any increase in number or activity of an immune cell, or an increase in expression or absolute levels of an immune factor, such as a cytokine. Immune cells include, but are not limited to, NK cells, CD4+T lymphocytes, CD8+T lymphocytes, B cells, dendritic cells, macrophage and other antigen-presenting cells.

As used herein, the term "CpG oligonucleotides," "immunostimulatory CpG nucleic acids" or "immunostimulatory CpG oligonucleotides" refers to any CpG-containing oligonucleotide that is capable of activating an immune cell. At least the C of the CpG dinucleotide is typically unmethylated. Immunostimulatory CpG oligonucleotides are described in a number of issued patents and published patent applications, including U.S. Pat. Nos. 6,194,388; 6,207,646; 6,218,371; 6,239,116; 6,339,068; 6,406,705; and 6,429,199.

In some embodiments, the CpG oligonucleotides are 4-100 nucleotides in length. In other embodiments, the CpG oligonucleotides are 4-90, 4-80, 4-70, 4-60, 4-50, 4-40, 4-30, 4-20, or 4-10 nucleotides in length.

In some embodiments the immunostimulatory oligonucleotides have a modified backbone such as a phosphorothioate (PS) backbone. In other embodiments the immunostimulatory oligonucleotides have a phosphodiester (PO) backbone. In yet other embodiments immunostimulatory oligonucleotides have a mixed PO and PS backbone. The CpG oligonucleotides may be A-class oligonucleotides, B-class oligonucleotides, or C-class oligonucleotides. "A-class" CpG immunostimulatory oligonucleotides have been described in published PCT application WO 01/22990. These oligonucleotides are characterized by the ability to induce high levels of interferon-alpha while having minimal effects on B cell activation. The A class CpG immunostimulatory nucleic acid may contain a hexamer palindrome GACGTC, AGCGCT, or AACGTT described by Yamamoto and colleagues. Yamamoto S et al. J Immunol 148:4072-6 (1992). Traditional A-class oligonucleotides have poly-G rich 5' and 3' ends and a palindromic center region. Typically the nucleotides at the 5' and 3' ends have stabilized internucleotide linkages and the center palindromic region has phosphodiester linkages (chimeric).

B class CpG immunostimulatory nucleic acids strongly activate human B cells but have minimal effects inducing interferon-α without further modification. Traditionally, the B-class oligonucleotides include the sequence 5' TCN$_1$TX$_1$X$_2$CGX$_3$X$_4$ 3', wherein X$_1$ is G or A; X$_2$ is T, G, or A; X$_3$ is T or C and X$_4$ is T or C; and N is any nucleotide, and N$_1$ and N$_2$ are nucleic acid sequences of about 0-25 N's each. B-class CpG oligonucleotides that are typically fully stabilized and include an unmethylated CpG dinucleotide within certain preferred base contexts are potent at activating B cells but are relatively weak in inducing IFN-α and NK cell activation. See, e.g., U.S. Pat. Nos. 6,194,388; 6,207,646; 6,214,806; 6,218,371; 6,239,116; and 6,339,068.

In one embodiment a B class CpG oligonucleotide is represented by at least the formula:

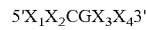
5'X$_1$X$_2$CGX$_3$X$_4$3' wherein X$_1$, X$_2$, X$_3$, and X$_4$ are nucleotides. In one embodiment X$_2$ is adenine, guanine, or thymine. In another embodiment X$_3$ is cytosine, adenine, or thymine.

In another embodiment the invention provides an isolated B class CpG oligonucleotide represented by at least the formula:

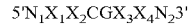
5'N$_1$X$_1$X$_2$CGX$_3$X$_4$N$_2$3' wherein X$_1$, X$_2$, X$_3$, and X$_4$ are nucleotides and N is any nucleotide and N$_1$ and N$_2$ are nucleic acid sequences composed of from about 0-25 N's each. In one embodiment $X_1X_2$ is a dinucleotide selected from the group consisting of: GpT, GpG, GpA, ApA, ApT, ApG, CpT, CpA, CpG, TpA, TpT, and TpG; and $X_3X_4$ is a dinucleotide selected from the group consisting of: TpT, ApT, TpG, ApG, CpG, TpC, ApC, CpC, TpA, ApA, and CpA. Preferably $X_1X_2$ is GpA or GpT and $X_3X_4$ is TpT. In other embodiments $X_1$ or $X_2$ or both are purines and $X_3$ or $X_4$ or both are pyrimidines or $X_1X_2$ is GpA and $X_3$ or $X_4$ or both are pyrimidines. In another preferred embodiment $X_1X_2$ is a dinucleotide selected from the group consisting of: TpA, ApA, ApC, ApG, and GpG. In yet another embodiment $X_3X_4$ is a dinucleotide selected from the group consisting of: TpT, TpA, TpG, ApA, ApG, GpA, and CpA. $X_1X_2$ in another embodiment is a dinucleotide selected from the group consisting of: TpT, TpG, ApT, GpC, CpC, CpT, TpC, GpT and CpG; $X_3$ is a nucleotide selected from the group consisting of A and T and $X_4$ is a nucleotide, but wherein when $X_1X_2$ is TpC, GpT, or CpG, $X_3X_4$ is not TpC, ApT or ApC.

In another preferred embodiment the CpG oligonucleotide has the sequence 5' $TCN_1TX_1X_2CGX_3X_4$ 3'. The CpG oligonucleotides of the invention in some embodiments include $X_1X_2$ selected from the group consisting of GpT, GpG, GpA and ApA and $X_3X_4$ is selected from the group consisting of TpT, CpT and TpC.

The C class immunostimulatory nucleic acids contain at least two distinct motifs have unique and desirable stimulatory effects on cells of the immune system. Some of these ODN have both a traditional "stimulatory" CpG sequence and a "GC-rich" or "B-cell neutralizing" motif. These combination motif nucleic acids have immune stimulating effects that fall somewhere between those effects associated with traditional "class B" CpG ODN, which are strong inducers of B cell activation and dendritic cell (DC) activation, and those effects associated A-class CpG ODN which are strong inducers of IFN-α and natural killer (NK) cell activation but relatively poor inducers of B-cell and DC activation. Krieg A M et al. (1995) *Nature* 374:546-9; Ballas Z K et al. (1996) *J Immunol* 157:1840-5; Yamamoto S et al. (1992) *J Immunol* 148:4072-6. While preferred class B CpG ODN often have phosphorothioate backbones and preferred class A CpG ODN have mixed or chimeric backbones, the C class of combination motif immune stimulatory nucleic acids may have either stabilized, e.g., phosphorothioate, chimeric, or phosphodiester backbones, and in some preferred embodiments, they have semi-soft backbones.

The stimulatory domain or motif is defined by a formula: 5' $X_1DCGHX_2$ 3'. D is a nucleotide other than C. C is cytosine. G is guanine. H is a nucleotide other than G.

$X_1$ and $X_2$ are any nucleic acid sequence 0 to 10 nucleotides long. $X_1$ may include a CG, in which case there is preferably a T immediately preceding this CG. In some embodiments DCG is TCG. $X_1$ is preferably from 0 to 6 nucleotides in length. In some embodiments $X_2$ does not contain any poly G or poly A motifs. In other embodiments the immunostimulatory nucleic acid has a poly-T sequence at the 5' end or at the 3' end. As used herein, "poly-A" or "poly-T" shall refer to a stretch of four or more consecutive A's or T's respectively, e.g., 5' AAAA 3' or 5' TTTT 3'.

As used herein, "poly-G end" shall refer to a stretch of four or more consecutive G's, e.g., 5' GGGG 3', occurring at the 5' end or the 3' end of a nucleic acid. As used herein, "poly-G nucleic acid" shall refer to a nucleic acid having the formula 5' $X_1X_2GGGX_3X_4$ 3' wherein $X_1$, $X_2$, $X_3$, and $X_4$ are nucleotides and preferably at least one of $X_3$ and $X_4$ is a G.

Some preferred designs for the B cell stimulatory domain under this formula comprise TTTTTCG, TCG, TTCG, TTTCG, TTTTCG, TCGT, TTCGT, TTTCGT, TCGTCGT.

The second motif of the nucleic acid is referred to as either P or N and is positioned immediately 5' to $X_1$ or immediately 3' to $X_2$.

N is a B-cell neutralizing sequence that begins with a CGG trinucleotide and is at least 10 nucleotides long. A B-cell neutralizing motif includes at least one CpG sequence in which the CG is preceded by a C or followed by a G (Krieg A M et al. (1998) Proc Natl Acad Sci USA 95:12631-12636) or is a CG containing DNA sequence in which the C of the CG is methylated. As used herein, "CpG" shall refer to a 5' cytosine (C) followed by a 3' guanine (G) and linked by a phosphate bond. At least the C of the 5' CG 3' must be unmethylated. Neutralizing motifs are motifs which has some degree of immunostimulatory capability when present in an otherwise non-stimulatory motif, but, which when present in the context of other immunostimulatory motifs serve to reduce the immunostimulatory potential of the other motifs.

P is a GC-rich palindrome containing sequence at least 10 nucleotides long. As used herein, "palindrome" and, equivalently, "palindromic sequence" shall refer to an inverted repeat, i.e., a sequence such as ABCDEE'D'C'B'A' in which A and A', B and B', etc., are bases capable of forming the usual Watson-Crick base pairs.

As used herein, "GC-rich palindrome" shall refer to a palindrome having a base composition of at least two-thirds G's and C's. In some embodiments the GC-rich domain is preferably 3' to the "B cell stimulatory domain". In the case of a 10-base long GC-rich palindrome, the palindrome thus contains at least 8 G's and C's. In the case of a 12-base long GC-rich palindrome, the palindrome also contains at least 8 G's and C's. In the case of a 14-mer GC-rich palindrome, at least ten bases of the palindrome are G's and C's. In some embodiments the GC-rich palindrome is made up exclusively of G's and C's.

In some embodiments the GC-rich palindrome has a base composition of at least 81% G's and C's. In the case of such a 10-base long GC-rich palindrome, the palindrome thus is made exclusively of G's and C's. In the case of such a 12-base long GC-rich palindrome, it is preferred that at least ten bases (83%) of the palindrome are G's and C's. In some preferred embodiments, a 12-base long GC-rich palindrome is made exclusively of G's and C's. In the case of a 14-mer GC-rich palindrome, at least twelve bases (86%) of the palindrome are G's and C's. In some preferred embodiments, a 14-base long GC-rich palindrome is made exclusively of G's and C's. The C's of a GC-rich palindrome can be unmethylated or they can be methylated.

In general this domain has at least 3 Cs and Gs, more preferably 4 of each, and most preferably 5 or more of each. The number of Cs and Gs in this domain need not be identical. It is preferred that the Cs and Gs are arranged so that they are able to form a self-complementary duplex, or palindrome, such as CCGCGCGG. This may be interrupted by As or Ts, but it is preferred that the self-complementarity is at least partially preserved as for example in the motifs CGACGTTCGTCG (SEQ ID NO: 4) or CGGCGCCGTGCCG (SEQ ID NO: 5). When complementarity is not preserved, it is preferred that the non-complementary base pairs be TG. In a preferred embodiment there are no more than 3 consecutive bases that are not part of the palindrome, preferably no more than 2, and most preferably only 1. In some embodiments the GC-rich palindrome includes at least one CGG trimer, at least one CCG trimer, or at least one CGCG tetramer.

In other embodiments the oligonucleotide is an inhibitory nucleic acid. The oligonucleotide that is an inhibitory nucleic acid may be, for instance, an siRNA or an antisense molecule that inhibits expression of a protein that will have a therapeutic effect. The inhibitory nucleic acids may be designed using routine methods in the art.

An inhibitory nucleic acid typically causes specific gene knockdown, while avoiding off-target effects. Various strategies for gene knockdown known in the art can be used to inhibit gene expression. For example, gene knockdown strategies may be used that make use of RNA interference (RNAi) and/or microRNA (miRNA) pathways including small interfering RNA (siRNA), short hairpin RNA (shRNA), double-stranded RNA (dsRNA), miRNAs, and other small interfering nucleic acid-based molecules known in the art. In one embodiment, vector-based RNAi modalities (e.g., shRNA expression constructs) are used to reduce expression of a gene in a cell. In some embodiments, therapeutic compositions of the invention comprise an isolated plasmid vector (e.g., any isolated plasmid vector known in the art or disclosed herein) that expresses a small interfering nucleic acid such as an shRNA. The isolated plasmid may comprise a specific promoter operably linked to a gene encoding the small interfering nucleic acid. In some cases, the isolated plasmid vector is packaged in a virus capable of infecting the individual. Exemplary viruses include adenovirus, retrovirus, lentivirus, adeno-associated virus, and others that are known in the art and disclosed herein.

A broad range of RNAi-based modalities could be employed to inhibit expression of a gene in a cell, such as siRNA-based oligonucleotides and/or altered siRNA-based oligonucleotides. Altered siRNA based oligonucleotides are those modified to alter potency, target affinity, safety profile and/or stability, for example, to render them resistant or partially resistant to intracellular degradation. Modifications, such as phosphorothioates, for example, can be made to oligonucleotides to increase resistance to nuclease degradation, binding affinity and/or uptake. In addition, hydrophobization and bioconjugation enhances siRNA delivery and targeting Other molecules that can be used to inhibit expression of a gene include anti sense nucleic acids (single or double stranded), ribozymes, peptides, DNAzymes, peptide nucleic acids (PNAs), triple helix forming oligonucleotides, antibodies, and aptamers and modified form(s) thereof directed to sequences in gene(s), RNA transcripts, or proteins. Antisense and ribozyme suppression strategies have led to the reversal of a tumor phenotype by reducing expression of a gene product or by cleaving a mutant transcript at the site of the mutation. Ribozymes have also been proposed as a means of both inhibiting gene expression of a mutant gene and of correcting the mutant by targeted trans-splicing.

Triple helix approaches have also been investigated for sequence-specific gene suppression. Triple helix forming oligonucleotides have been found in some cases to bind in a sequence-specific manner. Similarly, peptide nucleic acids have been shown to inhibit gene expression. Minor-groove binding polyamides can bind in a sequence-specific manner to DNA targets and hence may represent useful small molecules for suppression at the DNA level.

Other inhibitor molecules that can be used include antisense nucleic acids (single or double stranded). Antisense nucleic acids include modified or unmodified RNA, DNA, or mixed polymer nucleic acids, and primarily function by specifically binding to matching sequences resulting in modulation of peptide synthesis. Antisense nucleic acid binds to target RNA by Watson Crick base-pairing and blocks gene expression by preventing ribosomal translation of the bound sequences either by steric blocking or by activating RNase H enzyme. Antisense molecules may also alter protein synthesis by interfering with RNA processing or transport from the nucleus into the cytoplasm.

As used herein, the term "antisense nucleic acid" describes a nucleic acid that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence.

An inhibitory nucleic acid useful in the invention will generally be designed to have partial or complete complementarity with one or more target genes. The target gene may be a gene derived from the cell, an endogenous gene, a transgene, or a gene of a pathogen which is present in the cell after infection thereof. Depending on the particular target gene, the nature of the inhibitory nucleic acid and the level of expression of inhibitory nucleic acid (e.g. depending on copy number, promoter strength) the procedure may provide partial or complete loss of function for the target gene. Quantitation of gene expression in a cell may show similar amounts of inhibition at the level of accumulation of target mRNA or translation of target protein. "Inhibition of gene expression" refers to the absence or observable decrease in the level of protein and/or mRNA product from a target gene. "Specificity" refers to the ability to inhibit the target gene without manifest effects on other genes of the cell. The consequences of inhibition can be confirmed by examination of the outward properties of the cell or organism or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS). For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin. Depending on the assay, quantitation of the amount of gene expression allows one to determine a degree of inhibition which is greater than 10%, 33%, 50%, 90%, 95% or 99% as compared to a cell not treated according to the present invention. As an example, the efficiency of inhibition may be determined by assessing the amount of gene product in the cell: mRNA may be detected with a hybridization probe having a nucleotide sequence outside the region used for the inhibitory nucleic acid, or translated polypeptide may be detected with an antibody raised against the polypeptide sequence of that region.

An expression enhancing oligonucleotide as used herein is a synthetic oligonucleotide that encodes a protein. The synthetic oligonucleotide may be delivered to a cell such that it is used by a cells machinery to produce a protein based on the sequence of the synthetic oligonucleotide. The synthetic oligonucleotide may be, for instance, synthetic DNA or synthetic RNA. "Synthetic RNA" refers to a RNA produced through an in vitro transcription reaction or through artificial (non-natural) chemical synthesis. In some embodiments, a synthetic RNA is an RNA transcript. In some embodiments, a synthetic RNA encodes a protein. In some embodiments, the synthetic RNA is a functional RNA. In some embodiments, a synthetic RNA comprises one or more modified nucleotides. In some embodiments, a synthetic RNA is up to 0.5 kilobases (kb), 1 kb, 1.5 kb, 2 kb, 2.5 kb, 3 kb, 4 kb, 5 kb, 6 kb, 7 kb, 8 kb, 9 kb, 10 kb, 15 kb, 20 kb, 25 kb, 30 kb or more in length. In some embodiments, a synthetic RNA is in a range of 0.1 kb to 1 kb, 0.5 kb to 2 kb, 0.5 kb to 10 kb, 1 kb to 5 kb, 2 kb to 5 kb, 1 kb to 10 kb, 3 kb to 10 kb, 5 kb to 15 kb, or 1 kb to 30 kb in length.

A diagnostic oligonucleotide is an oligonucleotide that interacts with a cellular marker to identify the presence of the marker in a cell or subject. Diagnostic oligonucleotides are well known in the art and typically include a label or are otherwise detectable.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

EXAMPLES

Materials and Methods
Synthesis of Oligonucleotide-Lipophilic Moiety Conjugates

Lipophilic moiety conjugated oligonucleotides were synthesized in 5'- to 3'-direction using β-cyanoethyl phosphoramidite chemistry on appropriate solid supports. Syntheses were carried out on Mermade12 DNA/RNA synthesizer. After the synthesis, oligonucleotides were cleaved from the solid support and deprotected by standard protocols using ammonia solution, and purified by RP-HPLC. Oligonucleotide-lipophilic moiety conjugate concentrations were measured using UV absorbance at 260 nm. All the oligonucleotide conjugates synthesized were characterized by MALDI-TOF mass spectrometry for molecular mass.

Liposome Synthesis

Liposomes were synthesized by homogenization of 1,2-dioleoyl-sn-glycero-3-phosphocholine (DOPC) hydrated in phosphate buffered saline solution (PBS) (137 mM NaCl, 10 M phosphate, 2.7 mM KCl, pH 7.4, hyclone) using a homogenizer (Avestin). Liposome diameters (~20 nm) were measured using dynamic light scattering using a Malvern Zetasizer Nano (Malvern Instruments). Lipid concentration was determined using a phospholipid assay kit (Sigma).

SNA Synthesis and Characterization

Oligonucleotide-lipophilic moiety conjugates (see Table 1) were used to synthesize SNAs at various loadings (see Table 2). SNAs were formulated by mixing a molar excess of lipophilic moiety-oligonucleotide conjugate to a liposome in PBS and storing them overnight at 4° C. SNAs were analyzed using 0.5% agarose gel electrophoresis and staining with 0.5 μg/ml ethidium bromide and size-exclusion chromatography (SEC) on a SEC-4000 column (Phenomenex). Light transmission of SNAs was measured at 700 nm using a Cary100Bio UV/VIS Spectrophotometer (Agilent). SNA diameters were measured using dynamic light scattering using a Malvern Zetasizer Nano.

TABLE 1

Oligonucleotide sequences and modifications

| Oligo # | Seq ID No | Sequence and modifications | Molecular weight Calculated | Observed |
|---|---|---|---|---|
| 1 | 1 | T*C*G*T*C*G*T*T*T*T*G*T*C*G*T*T*T*T*G*T*C*G*T˄SP18˄SP18˄R1 | 9143 | 9143 |
| 2 | 1 | T*C*G*T*C*G*T*T*T*T*G*T*C*G*T*T*T*T*G*T*C*G*T˄SP18˄SP18˄R2 | 9086 | 9084 |
| 3 | 1 | T*C*G*T*C*G*T*T*T*T*G*T*C*G*T*T*T*T*G*T*C*G*T˄SP18˄SP18˄R4 | 9035 | 9058 |
| 4 | 1 | T*C*G*T*C*G*T*T*T*T*G*T*C*G*T*T*T*T*G*T*C*G*T˄SP18˄SP18˄R7 | 8804 | 8782 |
| 5 | 1 | T*C*G*T*C*G*T*T*T*T*G*T*C*G*T*T*T*T*G*T*C*G*T˄SP18˄SP18˄R8 | 8719 | 8704 |
| 6 | 1 | T*C*G*T*C*G*T*T*T*T*G*T*C*G*T*T*T*T*G*T*C*G*T˄SP18˄SP18˄R9 | 8746 | 8740 |
| 7 | 1 | T*C*G*T*C*G*T*T*T*T*G*T*C*G*T*T*T*T*G*T*C*G*T˄SP18˄SP18˄R10 | 8774 | 8782 |
| 8 | 1 | T*C*G*T*C*G*T*T*T*T*G*T*C*G*T*T*T*T*G*T*C*G*T˄SP18˄SP18˄R11 | 8733 | 8713 |
| 9 | 1 | T*C*G*T*C*G*T*T*T*T*G*T*C*G*T*T*T*T*G*T*C*G*T˄SP18˄SP18˄R12 | 8756 | 8742 |
| 10 | 1 | T*C*G*T*C*G*T*T*T*T*G*T*C*G*T*T*T*T*G*T*C*G*T˄SP18˄SP18˄X(R3)$_2$ | 8981 | 8985 |
| 11 | 1 | T*C*G*T*C*G*T*T*T*T*G*T*C*G*T*T*T*T*G*T*C*G*T˄SP18˄SP18˄X(R5)$_2$ | 9063 | 9078 |
| 12 | 1 | T*C*G*T*C*G*T*T*T*T*G*T*C*G*T*T*T*T*G*T*C*G*T˄SP18˄SP18˄X(R6)$_2$ | 9119 | 9123 |
| 13 | 1 | T*C*G*T*C*G*T*T*T*T*G*T*C*G*T*T*T*T*G*T*C*G*T˄SP18˄SP18˄X(R7)$_2$ | 9349 | 9359 |
| 14 | 1 | T*C*G*T*C*G*T*T*T*T*G*T*C*G*T*T*T*T*G*T*C*G*T˄SP18˄SP18˄X(R8)$_2$ | 9205 | 9183 |
| 15 | 1 | T*C*G*T*C*G*T*T*T*T*G*T*C*G*T*T*T*T*G*T*C*G*T˄SP18˄SP18˄X(R9)$_2$ | 9261 | 9250 |
| 16 | 1 | T*C*G*T*C*G*T*T*T*T*G*T*C*G*T*T*T*T*G*T*C*G*T˄SP18˄SP18˄X(R10)$_2$ | 9287 | 9302 |
| 17 | 1 | T*C*G*T*C*G*T*T*T*T*G*T*C*G*T*T*T*T*G*T*C*G*T˄SP18˄SP18˄X(R11)$_2$ | 9201 | 9197 |
| 18 | 1 | T*C*G*T*C*G*T*T*T*T*G*T*C*G*T*T*T*T*G*T*C*G*T˄SP18˄SP18˄X(R12)$_2$ | 9297 | 9272 |

TABLE 1-continued

Oligonucleotide sequences and modifications

| Oligo # | Seq ID No | Sequence and modifications | Molecular weight Calculated | Observed |
|---|---|---|---|---|
| 19 | 1 | T*C*G*T*C*G*T*T*T*G*T*C*G*T*T*T*G*T*C*G*T^SP18^SP18^Y(R3)$_3$ | 9419 | 9419 |
| 20 | 1 | T*C*G*T*C*G*T*T*T*G*T*C*G*T*T*T*G*T*C*G*T^SP18^SP18^Y(R7)$_3$ | 9966 | 9992 |
| 21 | 1 | T*C*G*T*C*G*T*T*T*G*T*C*G*T*T*T*G*T*C*G*T^SP18^SP18^Y(R8)$_3$ | 9755 | 9742 |
| 22 | 1 | T*C*G*T*C*G*T*T*T*G*T*C*G*T*T*T*G*T*C*G*T^SP18^SP18^Y(R12)$_3$ | 9894 | 9866 |
| 23 | 2 | T*C*G*T*T*C*G*T*C*G*A*C*G*A*A^SP18^SP18^R1 | 6234 | 6235 |
| 24 | 2 | T*C*G*T*T*C*G*T*C*G*A*C*G*A*A^SP18^SP18^R8 | 5814 | 5832 |
| 25 | 2 | T*C*G*T*T*C*G*T*C*G*A*C*G*A*A^SP18^SP18^AR9 | 5841 | 5851 |
| 26 | 2 | T*C*G*T*T*C*G*T*C*G*A*C*G*A*A^SP18^SP18^AR10 | 5869 | 5871 |
| 27 | 2 | T*C*G*T*T*C*G*T*C*G*A*C*G*A*A^SP18^SP18^X(R3)$_2$ | 6049 | 6083 |
| 28 | 2 | T*C*G*T*T*C*G*T*C*G*A*C*G*A*A^SP18^SP18^X(R5)$_2$ | 6157 | 6176 |
| 29 | 2 | T*C*G*T*T*C*G*T*C*G*A*C*G*A*A^SP18^SP18^X(R6)$_2$ | 6205 | 6233 |
| 30 | 2 | T*C*G*T*T*C*G*T*C*G*A*C*G*A*A^SP18^SP18^X(R7)$_2$ | 6411 | 6469 |
| 31 | 2 | T*C*G*T*T*C*G*T*C*G*A*C*G*A*A^SP18^SP18^X(R8)$_2$ | 6269 | 6290 |
| 32 | 2 | T*C*G*T*T*C*G*T*C*G*A*C*G*A*A^SP18^SP18^X(R9)$_2$ | 6325 | 9342 |
| 33 | 2 | T*G*G*T*T*C*G*T*C*G*A*C*G*A*A^SP18^SP18^X(R10)$_2$ | 6381 | 6413 |
| 34 | 2 | T*G*G*T*T*C*G*T*C*G*A*C*G*A*A^SP18^SP18^X(R11)$_2$ | 6295 | 6287 |
| 35 | 1 | T*C*G*T*C*G*T*T*T*G*T*C*G*T*T*T*G*T*C*G*T | 7698 | 7699 |
| 36 | 3 | mUmGmGmGmAmGT*A*G*A*C*A*mAmGmGmUmAmC^SP18^SP18^R1 | 7485 | 7487 |
| 37 | 3 | mUmGmGmGmAmGT*A*G*A*C*A*mAmGmGmUmAmC^SP18^SP18^X(R9)$_2$ | 7608 | 7543 |

Abbreviations

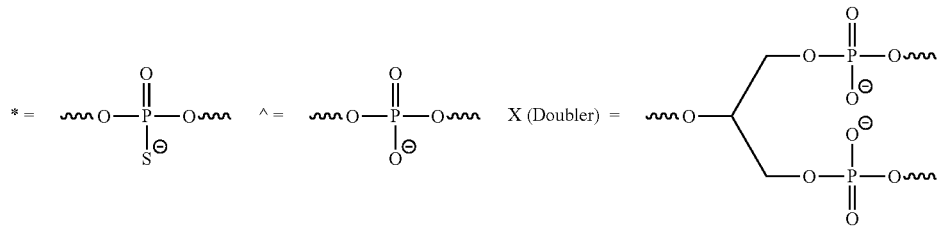

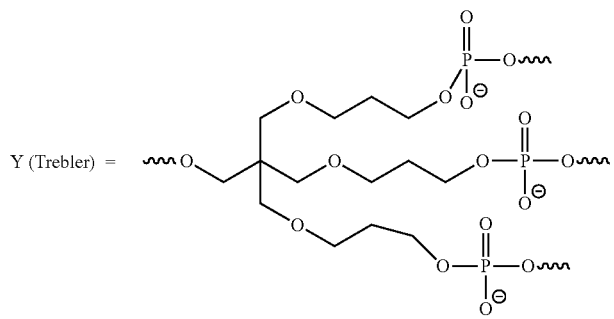

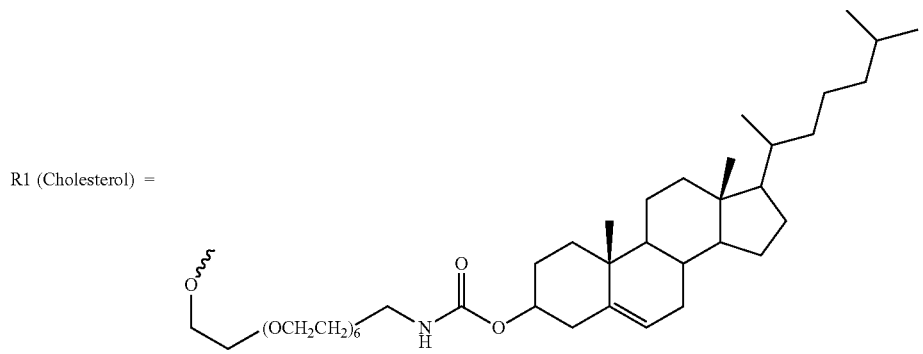

-continued

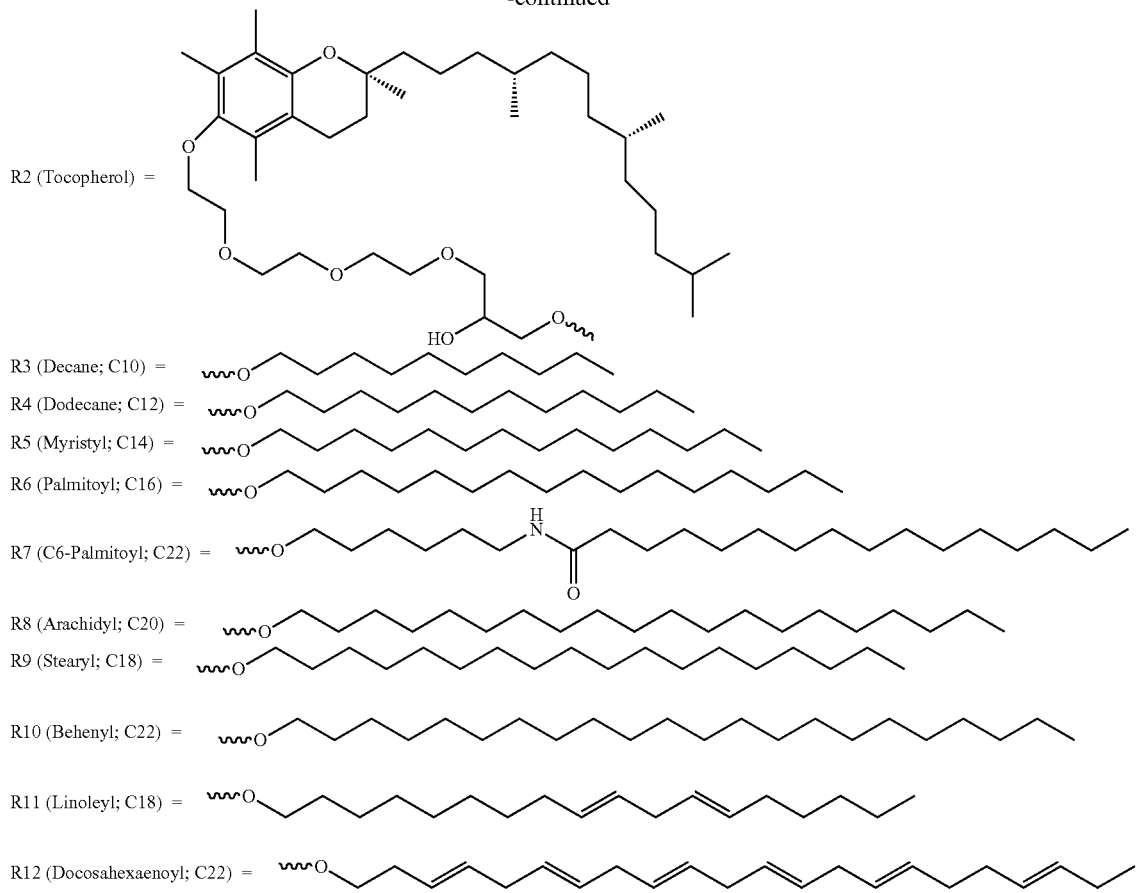

Spherical nucleic acid (SNA) using the oligonucleotides described herein were generated and assigned a SNA number (also referred to by a letter designation in the Figures and Table). The composition of each SNA compound is listed below in Table 3, identifying the oligo number and number of oligo's loaded on the surface.

TABLE 2

Spherical nucleic acid (SNA) constructs

| SNA# | Letter designation | Oligo sequence # | Approximate Oligo Loading per Particle |
|---|---|---|---|
| SNA1_10 | A | Oligo 1 | 10 |
| SNA1_20 | B | Oligo 1 | 20 |
| SNA1_25 | C | Oligo 1 | 25 |
| SNA1_30 | D | Oligo 1 | 25 |
| SNA1_50 | E | Oligo 1 | 25 |
| SNA 2 | F | Oligo 2 | 25 |
| SNA 3 | G | Oligo 3 | 0 |
| SNA 4 | H | Oligo 5 | 0 |
| SNA 5 | I | Oligo 6 | 0 |
| SNA 6 | J | Oligo 9 | 0 |
| SNA 7 | K | Oligo 11 | 25 |
| SNA 8 | L | Oligo 12 | 25 |
| SNA 9 | M | Oligo 13 | 25 |
| SNA 10 | N | Oligo 14 | 25 |
| SNA 11 | O | Oligo 15 | 25 |
| SNA 12 | P | Oligo 16 | 25 |
| SNA 13 | Q | Oligo 18 | 25 |
| SNA 14 | R | Oligo 20 | 25 |
| SNA 15 | S | Oligo 21 | 25 |

TABLE 2-continued

Spherical nucleic acid (SNA) constructs

| SNA# | Letter designation | Oligo sequence # | Approximate Oligo Loading per Particle |
|---|---|---|---|
| SNA 16 | T | Oligo 22 | 25 |
| SNA 17 | U | Oligo 23 | 30 |
| SNA 18_30 | V | Oligo 32 | 30 |
| SNA 18_50 | W | Oligo 32 | 50 |
| SNA 18_60 | X | Oligo 32 | 60 |
| SNA 18_70 | Y | Oligo 32 | 60 |
| SNA 18_80 | Z | Oligo 32 | 60 |
| SNA 18_90 | AA | Oligo 32 | 60 |
| SNA 18_100 | AB | Oligo 32 | 60 |
| SNA 19_30 | AC | Oligo 36 | 25 |
| SNA 20_30 | AD | Oligo 37 | 30 |
| SNA 20_60 | AE | Oligo 37 | 60 |

Human PBMC Cultures

Fresh human peripheral blood mononuclear cells (PBMCs) from five different donors (Zenbio) were cultured in RPMI supplemented with 10% fetal bovine serum, 2 mM L-glutamine, 50 U/mL penicillin, and 50 mg/mL streptomycin. Cells were maintained at 37° C. in a 5% $CO_2$ humidified incubator. SNAs were applied to PBMCs in 96-well tissue culture plates for 24 hours at concentrations listed in Table 4 and Table 5. After 24 hours of treatment, PBMC culture supernatants were collected for cytokine analysis.

TABLE 3

Characterization of SNAs with various oligonucleotide loading densities

| SNA# | Oligo Loading per Particle | Number Mean Diameter | Polydispersity (PDI) | Z-Average Diameter | @700 nm % Transmission |
|---|---|---|---|---|---|
| SNA17 | 25 | 831.5 | 0.404 | 1345.0 | 0.76 |
| SNA18_30 | 30 | 544.8 | 0.221 | 1260.3 | 2.58 |
| SNA18_60 | 60 | 27.6 | 0.223 | 54.2 | 97.3 |
| SNA19_30 | 25 | 2462.7 | 0.21 | 2358.3 | 1.5 |
| SNA20_30 | 30 | 26.6 | 0.42 | 121.1 | 41.5 |
| SNA20_60 | 60 | 36.6 | 0.36 | 104.6 | 72.8 |

TABLE 4

In vitro cytokine secretion in human PBMC cultures

Donor 1

| Compound[a] | IL-6 (pg/ml) | IL-12p70 (pg/mL) | TNFα (pg/mL) |
|---|---|---|---|
| PBS | 28.6 | 7.4 | 30.2 |
| SNA 1_30 | 1128.9 | 12.2 | 129.1 |
| SNA 2 | 558.0 | 12.1 | 59.7 |
| SNA 9 | 875.8 | 13.1 | 95.4 |
| SNA 10 | 1039.7 | 8.0 | 182.7 |
| SNA 13 | 782.7 | 12.9 | 55.7 |
| SNA 14 | 684.4 | 7.7 | 175.9 |
| SNA 16 | 474.2 | 11.1 | 71.8 |

| Compound[a] | IL-6 (pg/ml) | IL-12p70 (pg/mL) | TNFα (pg/mL) | IFNγ (pg/mL) |
|---|---|---|---|---|
| | | Donor 2 | | |
| PBS | 21.2 | 25.5 | 36.6 | 138.4 |
| SNA 1_30 | 997.3 | 75.9 | 221.6 | 245.3 |
| SNA 2 | 709.5 | 49.3 | 123.8 | 276.6 |
| SNA 9 | 955.0 | 69.2 | 267.4 | 236.5 |
| SNA 10 | 1336.8 | 27.2 | 411.4 | 271.3 |
| SNA 13 | 1395.4 | 25.6 | 122.2 | 268.6 |
| SNA 14 | 1057.9 | 25.5 | 283.5 | 356.7 |
| SNA 16 | 1236.5 | 53.6 | 318.8 | 264.1 |
| | | Donor 3 | | |
| PBS | 5 | 5 | 5 | 7 |
| SNA 1_30 | 367 | 249 | 65 | 23 |
| SNA 8 | 538 | 186 | 57 | 45 |
| SNA 9 | 382 | 232 | 57 | 24 |
| SNA 10 | 431 | 237 | 62 | 55 |
| SNA 11 | 503 | 167 | 71 | 69 |
| SNA 12 | 791 | 81 | 167 | 32 |

[a] At 2.5 µM oligonucleotide concentration

TABLE 5

In vitro cytokine secretion in human PBMC cultures with SNA 18_60

| Compound | IL-6 (pg/ml) [a] | IL-12p40 (pg/mL) [a] | TNFα (pg/mL) [a] | IFNα (pg/mL) [b] |
|---|---|---|---|---|
| | | Donor 1 | | |
| PBS | 28.3 | 6.82 | 16.69 | 6.38 |
| SNA 18_60 | 709.79 | 33.80 | 173.14 | 4642.07 |
| | | Donor 2 | | |
| PBS | 12.94 | 12.78 | 30.2 | 0.3 |
| SNA 18_60 | 529.58 | 176.67 | 376.0 | 3885.0 |

[a] At 3.33 µM oligonucleotide concentration
[b] At 0.123 µM oligonucleotide concentration
[a] At 5.00 µM oligonucleotide concentration
[b] At 0.312 µM oligonucleotide concentration Cytokine Induction in Mouse Serum Female, 6-week old C57BL6 mice were administered 7.5 mg/kg SNA subcutaneously. At 10 hours following SNA administration, serum was collected for cytokine analysis.

Cytokine Analysis Using Q-Plex Array

The cytokine levels in human PBMC culture supernatants and mouse seum were measured using a Q-Plex chemiluminescent arrays (Quansys) following the manufacturer's instructions. The plates were imaged using a Bio-Rad ChemiDoc XRS+ imager and the data were analyzed using the Q-view software (Quansys).

Results

Figure 2:
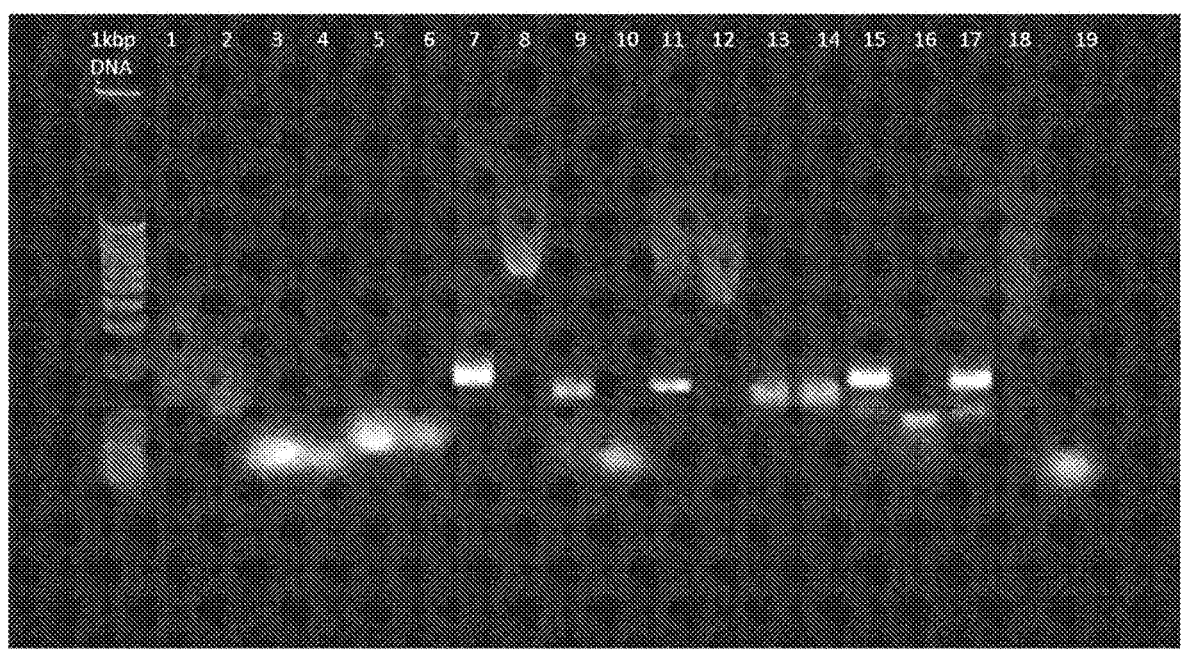
FIG. 2 depicts agarose gel electrophoresis of SNA constructs and oligonucleotide-lipophilic moiety conjugates. Gel electrophoresis of SNA4 (Lane 1), Oligo 5 (Lane 2), SNA 6 (Lane 3), Oligo 9 (Lane 4), SNA 5(Lane 5), Oligo 6 (Lane 6), SNA 10 (Lane 7), Oligo 14 (Lane 8), SNA 13 (Lane 9), Oligo 18 (Lane 10), SNA 8 (Lane 11), Oligo 12 (Lane 12), SNA 15 (Lane 13), Oligo 21 (Lane 14), SNA 16 (Lane 15), Oligo 22 (Lane 16), SNA 14 (Lane 17), Oligo 20 (Lane 18), Oligo 35 (Lane 19), using 0.5 agarose stained with 0.5 µg/ml ethidium bromide is shown. SNA formation is observed for SNA 10, SNA 13, SNA 8, SNA 15, SNA 16, and SNA 14, which have distinctive migrations compared to their respective constitutive lipophilic moiety-conjugated oligonucleotides.
Figure 3:
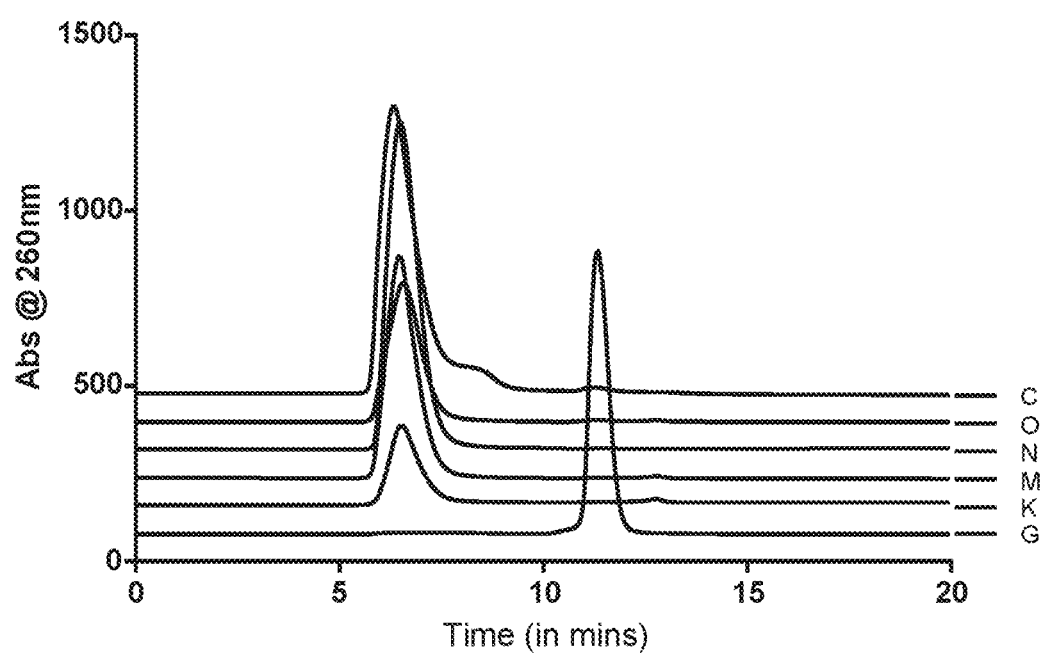
FIG. 3 shows size exclusion chromatography (SEC) analysis of SNAs functionalized with oligonucleotides with various lipophilic moieties. SNA 1_25, SNA 11, SNA 10, SNA 9, SNA 7, and SNA 3 were analyzed by SEC with PBS running buffer. SNA 3 shows elution of the unbound oligonucleotide only (11-12 minutes) with no SNA peak (6-7 minutes) indicating no self-assembly and formation of SNAs with the corresponding Oligo 3. SNA 1_25, SNA 11, SNA 10, SNA 9, and SNA 7, all elute at 6-7 minutes indicating self-assembly and SNA formation, with no free unbound lipophilic moiety-conjugated oligo.

Nature and Number of Lipophilic Moieties Conjugated to Oligonucleotide Determine SNA Assembly To determine the effect of the lipophilic moiety on SNA formation, SNAs were synthesized using oligonucleotide-lipophilic moiety conjugates listed in Table 1. Agarose gel electrophoresis was used to identify the formation of SNAs. Oligonucleotides conjugated to lipophilic moieties alone were run alongside the SNAs that were self-assembled with the same oligonucleotide. SNA formation results in a characteristic band which migrates between 1000-1500 bases which can be differentiated from the lipophilic moiety-conjugated oligonucleotide. It was observed that oligonucleotide conjugates of mono-alkyl lipophilic moieties did not form SNAs, but di- and tri-alkyl lipophilic moieties (≥C14) formed SNAs on DOPC liposomes (see FIG. 1 and FIG. 2). Further, size-exclusion chromatography (SEC) was used to characterize SNA formation from non-functionalized oligonucleotide-lipophilic moiety conjugates and observed that a mono-alkyl lipid moiety did not form SNA (SNA 3 through SNA 6) as demonstrated by late retention of the oligonucleotide-mono alkyl lipophilic moiety conjugate (11-12 mins). Mono-cholesterol- and di-alkyl lipophilic moiety-oligonucleotide conjugates formed SNAs as demonstrated by elution of the SNAs in the void volume (6-8 mins) (see FIG. 3).

Figure 4A:
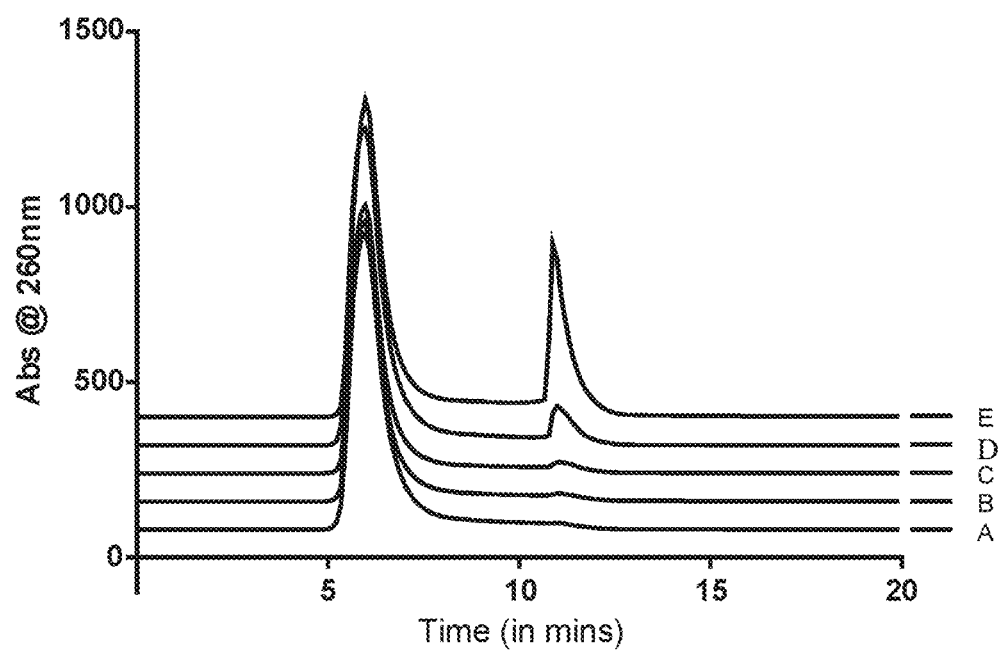
FIGS. 4A-4B show SEC analyses of oligonucleotide loading on SNA with various lipophilic moieties.
Figure 4B:
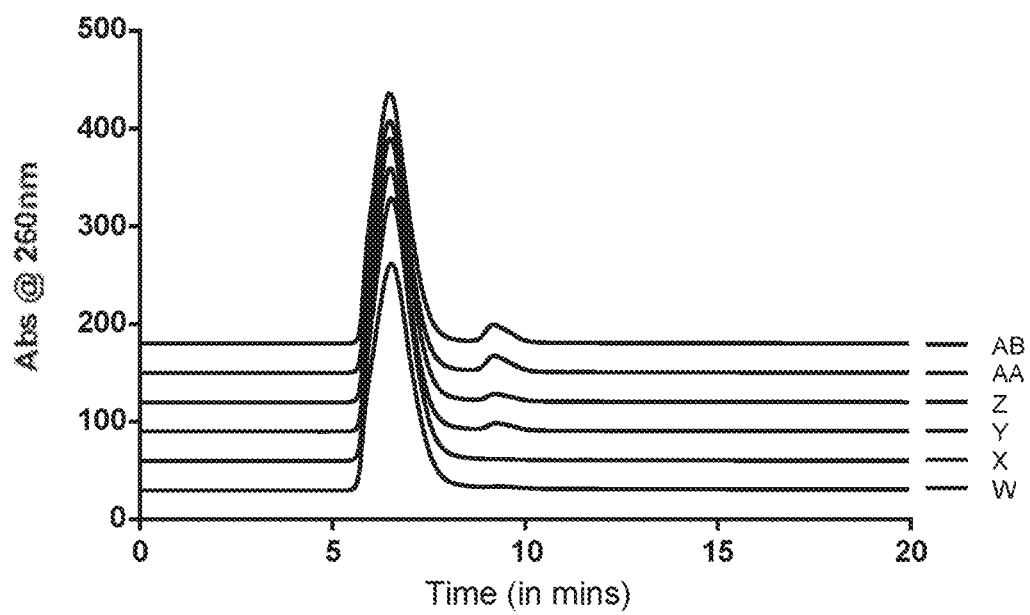

Oligonucleotide-Stearyl Lipophilic Moiety Conjugate Results in Higher SNA Loading Based on evidence of SNA formation determined using gel electrophoresis (FIGS. 1 and 2) it was sought to determine the loading capacities of oligonucleotide-lipophilic moieties per particle using SEC method. Oligonucleotide conjugates 1, 2, 11-16 and 18-22 with mono-cholesterol, mono-tocopherol, or different alkyl chain lipophilic moieties resulted in up to 25 oligonucleotides per particle (see FIG. 4A; Table 2). In contrast to other alkyl lipophilic moieties, cholesterol, and tocopherol, oligonucleotide-di-stearyl conjugates had the capability of loading up to 60-oligonucleotides per nanoparticle (see FIG. 4B).

Increased Loading Density Allows SNAs without Aggregation for Secondary Structure-Forming Oligonucleotides The oligonucleotide sequences 23-34 and 36-37 (see Table 1) have a self-complementary or a G-rich nucleotide sequence, respectively. Synthesis of SNAs with these oligonucleotide-cholesterol conjugates (25-oligonucleotides per particle) leads to aggregation of SNA to a suspension as determined by enlarged particle diameters and low light transmission (SNA 17 and SNA 19_30, see Table 3). This aggregation is inherent to SNAs that are synthesized with oligonucleotides that contain a self-complementary or a G-rich sequence that can potentially form secondary structures such as duplexes or G-quadruplexes, respectively, due to inter-particle interactions of oligonucleotides. When the self-complementary oligonucleotide was conjugated with a di-stearyl lipophilic moiety and synthesized SNA at 60-oligonucleotides per nanoparticle, the resulting SNAs did not aggregate as demonstrated by the small 27 nm particle diameter and high light transmission (SNA 18_60, see Table 3). However, loading of only 30-self-complementary oligonucleotide-di-stearyl moiety conjugates on liposomes resulted in SNA aggregation as in the case of cholesterol-oligonucleotide SNAs with enlarged particle diameters and low light transmission (SNA 18_30, see Table 3). Similarly, SNAs synthesized with G-rich oligonucleotide-di-stearyl moiety conjugates also at 60-oligonucleotides per nanoparticle abrogated aggregation significantly as demonstrated by the small 36.6 nm particle diameter and high light transmission (SNA 20_60, see Table 3). SNAs synthesized with a loading of only 30-oligonucleotides per nanoparticle of G-rich oligonucleotide-di-stearyl conjugates showed more aggregation than SNA 20_60, but less than that of cholesterol-oligonucleotide SNA 19_30 as demonstrated by decreased light transmission (SNA 20_30, see Table 3).

Immunostimulatory Activity of SNAs with Various Oligonucleotide-Lipophilic Moiety Conjugates Immunostimulatory activity of SNAs synthesized with a TLR9 stimulating oligonucleotide with various lipophilic moieties that formed SNAs was also evaluated. Human PBMCs from three different donors were treated with SNAs synthesized to characterize their cytokine release profiles. In general, SNAs exhibited similar cytokine induction profiles characteristic of TLR9 activation regardless of the type of lipophilic moiety conjugated to the oligonucleotide to synthesize the SNA (see Table 4). Self-complementary oligonucleotide sequence in SNA 18_60 is designed to elicit a strong IFNα response. As expected, SNA 18_60 stimulated IFNα induction in PBMCs from two different healthy human donors (see Table 5).

Cytokine induction in mouse serum following SNA administration was used to assess the in vivo immunostimulatory activity of SNAs with a TLR9 stimulating oligonucleotide and two different lipophilic moieties. SNAs with both lipophilic moieties induced similar cytokine profiles in mouse serum (see Table 6).

TABLE 6

| | In vivo cytokine induction in mouse serum | | | |
|---|---|---|---|---|
| Compound | IL-6 | IL-12p40 | MCP-1 | RANTES |
| PBS | 128 ± 0 | 73 ± 0 | 63 ± 1 | 68 ± 1 |
| SNA 1_25 | 1343 ± 292 | 159 ± 44 | 4389 ± 294 | 748 ± 118 |
| SNA 2 | 530 ± 53 | 270 ± 36 | 4300 ± 137 | 579 ± 77 |

Mean serum cytokine level (pg/mL) ± SEM of n = 4 mice per group

Together, these results demonstrate that multiple lipophilic moieties, including di- or tri-alkyl lipophilic moieties, conjugated to oligonucleotides permit synthesis of SNAs with desired characteristics without significant effect on their biological activity.

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

What is claimed is:

1. A nanostructure comprising:

a spherical nucleic acid (SNA) comprising a core, a lipid shell having an inner surface surrounding the core and an outer surface, and an oligonucleotide linked to a lipophilic moiety wherein the oligonucleotide is functionalized to the lipid shell through interaction between the lipid shell and at least a portion of the lipophilic moiety and the oligonucleotide is oriented radially outwards, wherein the lipophilic moiety is comprised of two or more lipophilic groups and has the following structure:

-L1-(Spacer)$_n$-L2-(Spacer)$_{n1}$-L3-X-(alkyl group)$_m$, wherein L1, L2, and L3 are each linkers and independent of one another are a phosphodiester or phosphorothioate bond or short chain linkage, wherein the spacer is an oligoethylene glycol spacer, wherein n and n1 are independently 0-3, wherein at least one of n and n1 is not 0, wherein X is a doubler or trebler, the alkyl group is a $C_6$-$C_{30}$ saturated or unsaturated alkyl group and m is 2-3, wherein the doubler and trebler have the following structures, respectively:

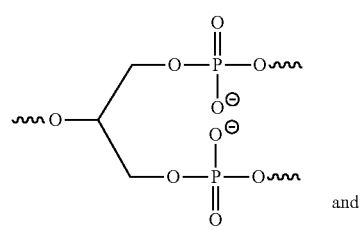

and

-continued

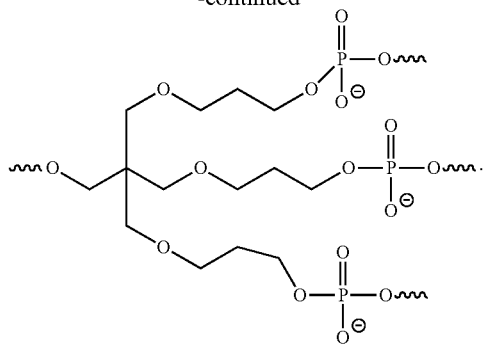

2. The nanostructure of claim 1, wherein the oligoethylene glycol spacer is a HEG spacer (hexaethylene glycol).

3. The nanostructure of claim 1, wherein L1, L2, and L3 are phosphodiester linkages.

4. The nanostructure of claim 1, wherein the lipid shell comprises 1,2-dioleoyl-sn-glycero-3-phophocholine (DOPC).

5. The nanostructure of claim 1, wherein the oligonucleotide is a single stranded oligonucleotide and/or an immunostimulatory oligonucleotide.

6. The nanostructure of claim 1, wherein the oligonucleotide is a self-aggregating oligonucleotide containing a self-complementary motif.

7. A composition of the nanostructures of claim 1.

8. The nanostructure of claim 1, wherein the oligonucleotide contains a G-rich motif.

9. The nanostructure of claim 1, wherein the oligonucleotide is an immunostimulatory oligonucleotide and/or an antisense oligonucleotide.

10. The nanostructure of claim 9, wherein the immunostimulatory oligonucleotide stimulates a toll-like receptor 9 (TLR9).

11. The nanostructure of claim 1, wherein the core is a hollow core or a solid core.

12. The composition of claim 7, wherein the composition has a polydispersity index (PDI) of 0.1-0.4.

13. The composition of claim 7, wherein the nanostructures have a Z average diameter of 30-1,300 nm.

* * * * *